(12) United States Patent
Wu

(10) Patent No.: US 6,436,717 B1
(45) Date of Patent: Aug. 20, 2002

(54) SYSTEM AND METHOD FOR OPTICAL CHEMICAL SENSING

(75) Inventor: Huan Ping Wu, Beavercreek, OH (US)

(73) Assignee: Yellow Springs Optical Sensor Co. PLL, Yellow Springs, OH (US)

( * ) Notice: Subject to any disclaimer, the term of this patent is extended or adjusted under 35 U.S.C. 154(b) by 0 days.

(21) Appl. No.: 09/509,299
(22) PCT Filed: May 12, 1999
(86) PCT No.: PCT/US99/10342
§ 371 (c)(1), (2), (4) Date: Mar. 23, 2000
(87) PCT Pub. No.: WO99/58961
PCT Pub. Date: Nov. 18, 1999

Related U.S. Application Data
(60) Provisional application No. 60/085,366, filed on May 13, 1998.

(51) Int. Cl.[7] .......................... G01N 21/59; G01N 21/64
(52) U.S. Cl. ...................... 436/133; 436/163; 436/172; 422/82.08; 422/82.09
(58) Field of Search .............................. 436/133, 163, 436/172; 422/82.05, 82.07, 82.08, 82.09, 82.11; 250/458.1, 459.1

(56) References Cited

U.S. PATENT DOCUMENTS

| | | |
|---|---|---|
| 4,200,110 A | 4/1980 | Peterson et al. |
| 4,476,870 A | 10/1984 | Peterson et al. |
| 4,548,907 A | 10/1985 | Seitz et al. |
| 4,833,091 A | 5/1989 | Leader et al. |
| 4,851,195 A | 7/1989 | Matthews et al. |
| 5,093,266 A | 3/1992 | Leader et al. |
| 5,094,959 A | 3/1992 | Allen et al. |
| 5,102,625 A | 4/1992 | Milo |
| 5,114,864 A | 5/1992 | Walt |
| 5,244,636 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,320,814 A | 6/1994 | Walt et al. |
| 5,403,746 A | 4/1995 | Bentsen et al. |
| 5,672,515 A | 9/1997 | Furlong |

OTHER PUBLICATIONS

Wolfbeis, Otto S. et al.—Fiber–Optic Fluorosensor for Oxygen and Carbon Dioxide, *Analytical Chemistry*, vol. 60, No. 19, Oct. 1, 1988—pp. 2028–2030.

Mills, Andrew et al.—Equilibrium Studies on Colorimetric Plastic Film Sensors for Carbon Dioxide, *Analytical Chemistry*, vol. 64, No. 13, Jul. 1, 1992—pp. 1383–1389.

Guillermo, Orellana et al.—Fiber–Optic Sensing of Carbon Dioxide Based on Excited–State Proton Transfer to a Luminescent Ruthenium (II) Complex, *Analytical Chemistry*, vol. 64, No. 19, Oct. 1, 1992—pp. 2210–2215.

DeGrandpre, Michael D.—Measure of Seawater $pCO_2$ Using a Renewable–Reagent Fiber Optic Sensor with Colorimetric Detection, *Analytical Chemistry*, vol. 65, No. 4, Feb. 15, 1993—pp. 331–337.

Parker, Jennifer W. et al.,—Fiber Optic Sensors for pH and Carbon Dioxide Using a Self–Referencing Dye, *Analytical Chemistry*, vol. 65, No. 17, Sep. 1, 1993—pp. 2329–2334.

Song, Antonios, et al.—High–Performance Fiber–Optic pH Microsensors for Practical Physiological Measurements Using a Dual–Emmission Sensitive Dye, *Analytical Chemistry*, vol. 69, No. 5, Mar. 1, 1997—pp. 863–867.

*Primary Examiner*—Jeffrey Snay
(74) *Attorney, Agent, or Firm*—Thompson Hine LLP

(57) ABSTRACT

The invention comprises a method for determining an analyte in which a dye solution is illuminated to induce a first and a second output light at a first and second wavelength, respectively, and the analyte concentration is determined from the measured first and second output intensities. The apparatus includes a probe (12) containing a dye solution, a light source (24), a frequency-sensitive photodetector (28) and a controller (90).

66 Claims, 16 Drawing Sheets

US 6,436,717 B1

SYSTEM AND METHOD FOR OPTICAL CHEMICAL SENSING

This is a national stage entry under 35 U.S.C. 371 of PCT/US99/10342, filed May 12, 1999, which claimed benefit of provisional application Serial No. 60/085,366, filed May 13, 1998.

FIELD OF THE INVENTION

The present invention is directed to a method and apparatus for optical chemical sensing and more particularly, to methods and systems for determining analyte contents of media by measuring spectral properties of a dye materials exposed to the analyte and processing the spectral properties in accordance with a family of ratiometric expressions.

BACKGROUND OF THE INVENTION

Various forms of analyte-measuring instruments have been designed and developed for use in biotechnology, industrial and environmental applications. Among these devices are those which rely on spectral properties of dye solutions responsive to a particular analyte. When a dye solution interacts with the analyte, the spectral properties of the dye solution change to a degree related to the concentration of the analyte in the surrounding medium. Thus, one may determine the analyte content in an analyte-containing medium by measuring the change in the spectral properties of the dye solution after the dye solution is exposed to the medium.

Two spectral properties of materials which have been used in optical chemical measurements are optical absorption and fluorescence. Absorption occurs when a material is illuminated and a portion of the illuminating light is neither transmitted through the material, scattered by it nor reflected from it. In the case of a layer of a solution, Beer's Law states that the amount of light energy thus absorbed by a solute in a solution will depend on the wavelength of the illuminating light, the concentration of the solute in the solution and the thickness of the solution layer:

$$A = \epsilon b C,$$

where "A" is the "absorbance," that is, the common logarithm of the ratio of the intensity of the illuminating light to the intensity of the absorbed light; "$\epsilon$" is the "molar absorptivity" of the solute; "b" is the thickness of the layer of the solution; and "C" is the concentration of the solute in the solution. Typically, the molar absorptivity will vary with the wavelength of the illuminating light, reaching maximum values at a so-called "peak absorption wavelengths" of the solute.

Fluorescence occurs when light energy is absorbed by the material and subsequently emitted as light energy of a different wavelength. In the case of a thin layer of a dilute aqueous solution, the intensity "F" of the fluorescent emission can be expressed as follows:

$$F = 2.3 P K \epsilon b C,$$

where "P" is the intensity of the illuminating light and K is the "quantum efficiency" of the solute. Like the molar absorptivity "$\epsilon$," the quantum efficiency will vary with the wavelength of the emitted light.

Certain prior art devices included sensor elements or probes in which aqueous dye solutions were trapped between analyte-permeable surfaces and distal ends of optical fibers. When the probes were exposed to analyte-containing media, analyte molecules diffused into the dye solutions. The dye solutions were illuminated at one or more selected wavelengths. The optical fibers gathered light returning from the dye solutions and conducted the light to one or more transducers. These transducers measured the intensities of the light to determine spectral properties of the dye solution. The spectral properties of the dye solutions were then used to determine the analyte content of the media.

Peterson et al. U.S. Pat. No. 4,200,110 proposed a fiber optic pH sensor using phenol red dye copolymerized with an acrylic base polymer to form microspheres. After the microspheres were exposed to a sample to be measured, they were illuminated sequentially by light at the peak excitation wavelength of the conjugate base (that is, a wavelength of illuminating light which maximizes the emitted intensity), given as 560 nm, and at an isosbestic wavelength (that is, a wavelength at which the optical absorbance of the dye microspheres was independent of the pH), given as 485 nm.

Peterson et al. taught that the pH of the sample could be determined from the intensity of the fluorescent emission of the microspheres measured after the microspheres were illuminated at the peak excitation wavelength of the conjugate base of the dye. In addition, they suggested normalizing this measured intensity by dividing it by the intensity of the fluorescent emission measured after the microspheres were illuminated at the isosbestic wavelength. FIG. 3 of Peterson et al. suggested that the correlation of the pH to this normalized intensity was approximately linear over a range from about pH 6.5 to about pH 7.5.

Seitz et al. U.S. Pat. No. 4,548,907 proposed a fluorescence-based optical sensor including 8-hydroxy-1,3,6-pyrenetrisulfonic acid [hereinafter "HPTS"] dye immobilized on an ion exchange membrane. After the immobilized HPTS dye was exposed to a sample to be measured, it was illuminated sequentially by monochromatic light at peak excitation wavelengths of the undissociated HPTS dye, given as 405 nm, and of its conjugate base [hereinafter "PTS$^-$"], given as 470 nm. The intensity of the fluorescent output of the dye when the dye was illuminated at each wavelength was measured using a photodetector having a narrow sensitivity band centered on 510 nm. A ratio was calculated by dividing the intensity of the fluorescent output of the dye after the dye was illuminated at the excitation wavelength of PTS$^-$, that is, at 470 nm, by the intensity of the fluorescent output of the dye after the dye was illuminated at the excitation wavelength of HPTS, that is, at 405 nm.

Seitz et al. taught that the correlation between the pH of the sample and the foregoing ratio could be treated as approximately linear over a range from about pH 6 to about pH 8. They recommended using this ratio to determine pH instead of the absolute value of a single measured intensity because the ratio was insensitive to factors such as source intensity variations, fluorescence quenching and degradation of the dye material.

Seitz et al. also proposed the use of their fluorescence-based optical sensor for measuring dissolved carbon dioxide in accordance with the so-called "Severinghouse" method. More particularly, they proposed measuring dissolved carbon dioxide in a sample by exposing the HPTS to a solution of sodium bicarbonate of known concentration which, in turn, was exposed to the sample. Carbonic acid ions from the sample tended to lower the pH of the sodium bicarbonate solution. Seitz et al. taught that, by using their optical sensor to measure the pH of the sodium bicarbonate solution, they could determine the concentration of dissolved carbon dioxide in the sample.

Peterson et al. U.S. Pat. No. 4,476,870 proposed a fiber optic probe for determining the partial pressure of oxygen in blood by measuring the fluorescence quenching of a suitable dye exposed to a sample to be measured. More specifically, the dye was exposed to the sample and illuminated with blue light. The intensity of the fluorescent output from the dye, measured in the green range, was correlated to the partial pressure of oxygen by the following formula:

$$P_{O_2} = P' \left[ \left( \frac{I_{blue}}{I_{green}} \right)^m - 1 \right]^n,$$

where "$P_{O_2}$" was the partial pressure of oxygen; "$I_{blue}$" was the intensity of the blue illuminating light; "$I_{green}$" was the intensity of the green fluorescent emission; "P'" was a constant having the dimensions of pressure; and "m" and "n" were non-dimensional constants.

One particularly demanding application for a chemical sensor is the measurement of the partial pressure of dissolved carbon dioxide in sea water. An oceanographic sensor may be called on to resolve differences in $CO_2$ partial pressure of as little as 1–2 ppm. The sensor must be compatible chemically with sea water and capable of providing accurate measurements despite relatively wide temperature variations.

Dr. David R. Walts of Tufts University proposed an oceanographic sensor in which dissolved $CO_2$ is detected in sea water by means of fluorescent emission intensity measurements performed on an aqueous solution of carboxyseminapthofluorescein [hereinafter "c-SNAFL"] exposed to the sea water through a gas permeable membrane. The c-SNAFL solution was excited by light at a wavelength of 488 nm and the intensities of the fluorescent emissions from the c-SNAFL solution were measured at wavelengths of approximately 545 nm and 625 nm. A non-linear relationship was found to exist between a simple ratio of the fluorescence intensities, $F_{545\ nm}/F_{625\ nm}$, and the $CO_2$ partial pressure over a range of about 0–1,000 ppm $CO_2$.

Additional optical chemical sensors were proposed in Furlong U.S. Pat. No. 5,672,515; Walt U.S. Pat. No. 5,252,494; Walt U.S. Pat. No. 5,114,864; Leader et al. U.S. Pat. No. 5,093,266; Matthews et al. U.S. Pat. No. 4,851,195; and Leader et al. U.S. Pat. No. 4,833,091.

Despite such proposals, there remains a need in the art for an optical chemical sensing method and system in which a strong linear correlation between the analyte content and a known function of the spectral properties of the dye solution promotes high resolution over a wide range of analyte content. At the same time, it is desired that the effects of factors, such as illumination intensity variations and photobleaching of the dye material, on the accuracy of the sensor system be minimized.

SUMMARY OF THE INVENTION

The present invention is directed to an optical chemical sensing method and system for determining an analyte content of a medium, particularly an aqueous medium. As used herein, the term "analyte content" is not intended to refer to a particular measure (such as concentration or partial pressure) but rather to any quantity denoting a relationship of the analyte to the medium as a whole. Examples of such quantities are the pH of an aqueous solution and the partial pressure of carbon dioxide on a fluid.

More particularly, the method and system of the invention determine the analyte content of a medium as a function of the spectral properties of a dye solution. Preferred dye solutions comprise dyes which dissociate to form conjugate ions having spectral properties different than those of the undissociated dye molecules. Changes in hydrogen ion concentration triggered by exposure of the dye solution to the analyte shift the equilibrium of the dissociation reaction, thereby altering the overall spectral properties of the dye solution. The analyte content may be determined as a function of the hydrogen ion concentration in the vicinity of the dye solution, which, in turn, preferably is determined as a ratio of linear combinations of spectral properties of the dye solution measured at two different wavelengths.

Thus, a preferred method in accordance with the present invention comprises the steps of exposing the dye solution to the analyte; illuminating the dye material to induce a first output light from said dye solution corresponding to a first wavelength and a second output light from said dye solution corresponding to a second wavelength; measuring an intensity of the first output light to determine a first spectral property "$X_1$;" measuring an intensity of the second output light to determine a second spectral property "$X_2$;" and processing the first and second spectral properties according to an expression of the form:

$$Y_{analyte} = f([H^+]) = f\left( k_1 k_2 - \frac{X_1 - k_3 X_2}{X_2 - k_4 X_1} \right),$$

where "$Y_{analyte}$" is the analyte content of the medium: "f" is a function which relates the hydrogen ion content in the vicinity of the dye solution to the analyte content of the medium; "$k_1$" is a constant which preferably depends primarily on the chemical properties of the dye; and "$k_2$," "$k_3$" and "$k_4$" are constants which preferably depend primarily on spectral properties of the undissociated dye molecules and the conjugate ions.

For present purposes, an expression of the form:

$$\frac{X_1 - k_3 X_2}{X_2 - k_4 X_1}$$

will be referred to as a "complex ratio," as distinguished from a "simple ratio" of the form $X_1/X_2$.

Preferred dye solutions for use in the method of the invention include dilute aqueous solutions of weakly acidic dyes such as HPTS and c-SNAFL. Where the dye is a weak acid, the constant $k_1$ is preferably the dissociation constant of the dye.

One especially preferred method in accordance with the invention uses a weakly acidic dye for measuring the pH of an aqueous medium. By definition, pH=−log[H⁺]. Applying this function of [H⁺] to the complex ratiometric expression given earlier:

$$pH = pK_a - \log\left( k_2 \frac{X_1 - k_3 X_2}{X_2 - k_4 X_1} \right),$$

where $pK_a \equiv -\log K_a$, "$K_a$" being the dissociation constant of the dye.

Another especially preferred method in accordance with the invention uses a dye material comprising an aqueous solution including a weakly acidic dye and an $HCO_3^-$ source to measure the partial pressure of carbon dioxide on a medium. In an aqueous solution, dissolved carbon dioxide reacts with water to form carbonic acid, which dissociates into hydrogen ions and bicarbonate:

The degree to which this reaction occurs at equilibrium will depend on the concentration of dissolved hydrogen ions in the solution:

$$\frac{[H^+][HCO_3^-]}{[CO_2]} = K_{a1},$$

where "$K_{a1}$" is the reaction constant for carrying out this reaction in aqueous solution. Rearranging this equation:

$$[CO_2] = \frac{[HCO_3^-]}{K_{a1}}[H^+].$$

Henry's law states that the concentration of a gas dissolved in a solution is proportional to the partial pressure of the gas. Applying Henry's Law to the previous equation yields:

$$P_{CO_2} = \frac{[CO_2]}{K_H} = \frac{1}{K_H K_{a1}}[HCO_3^-][H^+].$$

where "$P_{CO_2}$" is the partial pressure of carbon dioxide and "$K_H$" is the Henry's Law constant. Applying this function of $[H^+]$ to the complex ratiometric expression given earlier:

$$P_{CO_2} = \frac{K_a}{K_H K_{a1}}[HCO_3^-]\left(k_2\frac{X_1 - k_3 X_2}{X_2 - k_4 X_1}\right).$$

Measurements performed on test solutions have shown very strong linear correlations between the pH and $P_{CO_2}$ values of the test solutions, on the one hand, and the values derived from complex ratiometric expressions of the form set forth above, on the other. Experiments performed on batch solutions of c-SNAFL and $HCO_3^-$ indicate that resolutions of the order of magnitude of parts per million might be obtained over a range of carbon dioxide partial pressures on the order of 0–2,000 ppm. These results suggest that methods within the scope of the present invention are capable of the resolutions necessary for oceanographic $CO_2$ measurements.

A preferred sensor system for use in accordance with the present invention includes a sensor element or probe containing the dye material; at least one light source in optical communication with the probe for illuminating the dye material; at least one frequency-sensitive photodetector for measuring the intensity of light output from the probe to determine a first spectral property "$X_1$" of the dye corresponding to a first wavelength and a second spectral property "$X_2$" corresponding to a second wavelength; and a controller for processing the first and second spectral properties to determine the analyte content in accordance with an expression of the form:

$$Y_{analyte} = f([H^+]) = f\left(k_1 k_2 \frac{X_1 - k_3 X_2}{X_2 - k_4 X_1}\right),$$

where "$Y_{analyte}$" is the analyte content of the medium; "f" is a function which relates the hydrogen ion content in the vicinity of the dye solution to the analyte content of the medium; and "$k_1$," "$k_2$," "$k_3$" and "$k_4$" are constants.

One advantage of the present invention is that it provides a straightforward mode of calibration. The coefficients "$k_2$," "$k_3$" and "$k_4$" are preferably each ratios of spectral properties of the undissociated dye molecules and the conjugate ions. Thus, a system in accordance with the invention may be calibrated merely by determining the spectral properties of the dye solution corresponding to the first and second wavelengths of light when the dye solution is exposed to buffer solutions of very high pH and very low pH. Since the method of the invention relates the analyte content of the medium to spectral properties of the dye material through a ratiometric expression, it can be anticipated that the system will be relatively insensitive to potential errors due to variations in the intensity of the illuminating light and to photobleaching of the dye solution.

Without wishing to be bound by any theory of operation, it is believed that, where a weakly acidic dye solution is used, the undissociated dye molecules, "HB," reach an equilibrium with the conjugate base ions, "$B^-$:"

$$HB = H^+ + B^-.$$

The degree to which this dissociation occurs at equilibrium will depend on the concentration of dissolved hydrogen ions in the vicinity of the dye solution:

$$\frac{[H^+][B^-]}{[HB]} = K_a.$$

Rearranging this equation:

$$[H^+] = K_a \frac{[HB]}{[B^-]}.$$

Note that the sum $C^{HB} \equiv [HB]+[B^-]$, that is, the total amount of dye added to the solution, remains constant independently of the concentration of dissolved hydrogen ions in the vicinity of the dye solution.

In accordance with one embodiment, analyte content is determined using absorbances of the dye solution measured after a thin layer of the dye solution is exposed to the analyte and illuminated at first and second wavelengths of light. It is assumed that only the undissociated dye molecules and their conjugate base ions contribute to the absorbance of the dye solution. Then, the absorbance of the thin layer of the dye solution will be expressible in accordance with Beer's Law:

$$A_1 = A^{HB}_1 + A^{B^-}_1 = \epsilon^{HB}_1 b[HB] + \epsilon^{B^-}_1 b[B^-]$$

$$A_2 = A^{HB}_2 + A^{B^-}_2 = \epsilon^{HB}_2 b[HB] + \epsilon^{B^-}_2 b[B^-]$$

where:
"$A_1$" is the absorbance measured after the dye solution is illuminated by the first illumination wavelength;
"$A^{HB}_1$" is that part of the absorbance, measured after the dye solution is illuminated by the first illumination wavelength, which is attributable to the undissociated dye molecule in the solution;
"$A^{B^-}_1$" is that part of the absorbance, measured after the dye solution is illuminated by the first illumination wavelength, which is attributable to the conjugate base ion in the solution;
"$\epsilon^{HB}_1$" is the molar absorptivity of the undissociated dye molecule corresponding to the first illumination wavelength;
"b" is the thickness of the dye solution layer;
"$\epsilon^{B^-}_1$" is the molar absorptivity of the conjugate base ion corresponding to the first illumination wavelength; and
"$A_2$," "$A^{HB}_2$," "$A^{B^-}_2$," "$\epsilon^{HB}_2$" and "$\epsilon^{B^-}_2$" are analogous quantities measured with respect to illumination of the dye solution at the second illumination wavelength.

Since the foregoing equations are linear, they can be solved to express the concentrations as linear functions of the measured absorbances as follows:

$$[HB] = \frac{\epsilon_2^{B^-}/b}{\epsilon_1^{HB}\epsilon_2^{B^-} - \epsilon_2^{HB}\epsilon_1^{B^-}} A_1 - \frac{\epsilon_1^{B^-}/b}{\epsilon_1^{HB}\epsilon_2^{B^-} - \epsilon_2^{HB}\epsilon_1^{B^-}} A_2;$$

$$[B^-] = \frac{\epsilon_1^{HB}/b}{\epsilon_1^{HB}\epsilon_2^{B^-} - \epsilon_2^{HB}\epsilon_1^{B^-}} A_2 - \frac{\epsilon_2^{HB}/b}{\epsilon_1^{HB}\epsilon_2^{B^-} - \epsilon_2^{HB}\epsilon_1^{B^-}} A_1.$$

Thus:

$$[H^+] = K_a \frac{[HB]}{[B^-]} = K_a \frac{\epsilon_2^{B^-} A_1 - \epsilon_1^{B^-} A_2}{\epsilon_1^{HB} A_2 - \epsilon_2^{HB} A_1}.$$

When the dye solution is exposed to a buffer solution having a high pH, all but a negligible amount of the dye will dissociate to form the conjugate base. Under these conditions, the remaining undissociated dye molecules will not absorb a significant amount of light. The absorbance of the dye solution then will take approximately the following form:

$$(A_1)_{high\ pH} = (A^{B^-}_1)_{high\ pH} = \epsilon_1^{B^-} b C^{HB};$$

$$(A_2)_{high\ pH} = (A^{B^-}_2)_{high\ pH} = \epsilon_2^{B^-} b C^{HB}.$$

Rearranging terms:

$$\epsilon_1^{B^-} = \frac{(A_1)_{high\ pH}}{bC^{HB}};$$

$$\epsilon_2^{B^-} = \frac{(A_2)_{high\ pH}}{bC^{HB}}.$$

When the dye solution is exposed to a buffer solution having a low pH, only a negligible amount of the dye will dissociate to form the conjugate base. Under these conditions, the remaining conjugate base ions will not absorb a significant amount of light. The absorbance of the dye solution then will take approximately the following form:

$$(A_1)_{low\ pH} = (A^{HB}_1)_{low\ pH} = \epsilon_1^{HB} b C^{HB};$$

$$(A_2)_{low\ pH} = (A^{HB}_2)_{low\ pH} = \epsilon_2^{HB} b C^{HB}.$$

Rearranging terms:

$$\epsilon_1^{HB} = \frac{(A_1)_{low\ pH}}{bC^{HB}};$$

$$\epsilon_2^{HB} = \frac{(A_2)_{low\ pH}}{bC^{HB}}.$$

Substituting these values into the expression for the concentration of dissolved hydrogen ions:

$$[H^+] = K_a \frac{(A_2)_{high\ pH} A_1 - (A_1)_{high\ pH} A_2}{(A_1)_{low\ pH} A_2 - (A_2)_{low\ pH} A_1}$$

$$= K_a \left[\frac{(A_2)_{high\ pH}}{(A_1)_{low\ pH}}\right] \frac{A_1 - \left[\frac{(A_1)_{high\ pH}}{(A_2)_{high\ pH}}\right] A_2}{A_2 - \left[\frac{(A_2)_{low\ pH}}{(A_1)_{low\ pH}}\right] A_1}.$$

As discussed earlier, the present invention determines analyte content in a medium as a function of hydrogen ion concentration near the dye material. Otherwise stated:

$$Y_{analyte} = f([H^+]) = f\left(K_a \left[\frac{(A_2)_{high\ pH}}{(A_1)_{low\ pH}}\right] \frac{A_1 - \left[\frac{(A_1)_{high\ pH}}{(A_2)_{high\ pH}}\right] A_2}{A_2 - \left[\frac{(A_2)_{low\ pH}}{(A_1)_{low\ pH}}\right] A_1}\right).$$

In accordance with another embodiment, analyte content is determined using fluorescent emission intensities of the dye solution corresponding to first and second wavelengths of light. It is assumed that the dye solution is dilute and that only the undissociated dye molecules and their conjugate base ions contribute to the fluorescent emission of the dye solution. Then, the fluorescent emission of a thin layer of the dye solution will be expressible as follows:

$$F_1 = F^{HB}_1 + F^{B^-}_1 = 2.3 P_1 K^{HB}_1 \epsilon^{HB}_1 b[HB] + 2.3 P_1 K^{B^-}_1 \epsilon^{B^-}_1 b[B^-];$$

$$F_2 = F^{HB}_2 + F^{B^-}_2 = 2.3 P_2 K^{HB}_2 \epsilon^{HB}_2 b[HB] + 2.3 P_2 K^{B^-}_2 \epsilon^{B^-}_2 b[B^-];$$

where:
"$F_1$" is the intensity of the fluorescent emission corresponding to a first wavelength;
"$F^{HB}_1$" is that part of the intensity of the fluorescent emission corresponding to the first wavelength which is attributable to the undissociated acid molecule in the dye solution;
"$F^{B^-}_1$" is that part of the intensity of the fluorescent emission corresponding to the first wavelength which is attributable to the conjugate base ions in the dye solution;
"$P_1$" is the intensity of the illuminating light corresponding to the first wavelength;
"$K^{HB}_1$" is the quantum efficiency of the undissociated dye molecules corresponding to the first wavelength;
"$K^{B^-}_1$" is the quantum efficiency of the conjugate base ions corresponding to the first wavelength; and
"$F_2$," "$F^{HB}_2$," "$F^{b-}_2$," "$P_2$," "$K^{HB}_2$," and "$K^{B^-}_2$" are analogous quantities corresponding with a second wavelength.

Since the equations are linear, they can be solved to express the concentrations as linear functions of normalized fluorescent emission intensities (that is, the ratio of the fluorescent emission intensity divided by the illumination intensity) as follows:

$$[HB] = \frac{K_2^{B^-} \epsilon_2^{B^-}/2.3b}{K_1^{HB}\epsilon_1^{HB}K_2^{B^-}\epsilon_2^{B^-} - K_2^{HB}\epsilon_2^{HB}K_1^{B^-}\epsilon_1^{B^-}} (F_1/P_1) -$$

$$\frac{K_1^{B^-} \epsilon_1^{B^-}/2.3b}{K_1^{HB}\epsilon_1^{HB}K_2^{B^-}\epsilon_2^{B^-} - K_2^{HB}\epsilon_2^{HB}K_1^{B^-}\epsilon_1^{B^-}} (F_2/P_2);$$

$$[B^-] = \frac{K_1^{HB} \epsilon_1^{HB}/2.3b}{K_1^{HB}\epsilon_1^{HB}K_2^{B^-}\epsilon_2^{B^-} - K_2^{HB}\epsilon_2^{HB}K_1^{B^-}\epsilon_1^{B^-}} (F_2/P_2) -$$

$$\frac{K_2^{HB} \epsilon_2^{HB}/2.3b}{K_1^{HB}\epsilon_1^{HB}K_2^{B^-}\epsilon_2^{B^-} - K_2^{HB}\epsilon_2^{HB}K_1^{B^-}\epsilon_1^{B^-}} (F_1/P_1).$$

Thus:

$$[H^+] = K_a \frac{[HB]}{[B^-]} = K_a \frac{K_2^{B^-}\epsilon_2^{B^-} F_1/P_1 - K_1^{B^-}\epsilon_1^{B^-} F_2/P_2}{K_1^{HB}\epsilon_1^{HB} F_2/P_2 - K_2^{HB}\epsilon_2^{HB} F_1/P_1}.$$

After calibration with buffer solutions of high pH and low pH, respectively, the products of the molar absorptivitys and the quantum efficiencies will take approximately the form:

$$K_1^{B^-} \epsilon_1^{B^-} = \frac{(F_1/P_1)_{high\ pH}}{bC^{HB}};$$

$$K_2^{B^-} \epsilon_2^{B^-} = \frac{(F_2/P_2)_{high\ pH}}{bC^{HB}};$$

$$K_1^{HB} \epsilon_1^{HB} = \frac{(F_1/P_1)_{low\ pH}}{bC^{HB}};$$

$$K_2^{HB} \epsilon_2^{HB} = \frac{(F_2/P_2)_{low\ pH}}{bC^{HB}}.$$

Substituting these values into the expression for the concentration of dissolved hydrogen ions:

$$[H^+] = K_a \frac{(F_2/P_2)_{high\ pH} F_1/P_1 - (F_1/P_1)_{high\ pH} F_2/P_2}{(F_1/P_1)_{low\ pH} F_2/P_2 - (F_2/P_2)_{low\ pH} F_1/P_1}$$

$$= K_a \left[\frac{(F_2/P_2)_{high\ pH}}{(F_1/P_1)_{low\ pH}}\right] \left(\frac{F_1/P_1 - \left[\frac{(F_1/P_1)_{high\ pH}}{(F_2/P_2)_{high\ pH}}\right] F_2/P_2}{F_2/P_2 - \left[\frac{(F_2/P_2)_{low\ pH}}{(F_1/P_1)_{low\ pH}}\right] F_1/P_1}\right).$$

Since the present invention determines analyte content in a medium as a function of hydrogen ion concentration near the dye material:

$$Y_{analyte} = f\left(K_a \left[\frac{(F_2/P_2)_{high\ pH}}{(F_1/P_1)_{low\ pH}}\right] \frac{F_1/P_1 - \left[\frac{(F_1/P_1)_{high\ pH}}{(F_2/P_2)_{high\ pH}}\right] F_2/P_2}{F_2/P_2 - \left[\frac{(F_2/P_2)_{low\ pH}}{(F_1/P_1)_{low\ pH}}\right] F_1/P_1}\right).$$

In the case of a sensor using optical absorption measurements to determine analyte content, the first and second illumination wavelengths are most preferably the peak absorption wavelengths of the undissociated dye molecules and their conjugate base ions, respectively. In the case of a sensor using fluorescence emission measurements to determine analyte content, the dye solution is most preferably illuminated by the peak excitation frequencies of the undissociated dye molecule and its conjugate base. Illumination of the dye material at these frequencies likely will maximize the intensity of the light returning from the dye material which, in turn, likely will increase the resolution.

In the case of a pH sensor, $pH \equiv -\log[H^+]$. Thus, the following modifications of the Henderson-Hasselbach equation relate pH values in a medium of interest to absorbance and to normalized fluorescence emission measurements obtained in accordance with the present invention:

$$pH = pK_a + \log\left(\left[\frac{(A_1)_{low\ pH}}{(A_2)_{high\ pH}}\right] \frac{A_2 - \frac{(A_2)_{low\ pH}}{(A_1)_{low\ pH}} A_1}{A_1 - \frac{(A_1)_{high\ pH}}{(A_2)_{high\ pH}} A_2}\right),$$

and:

$$pH = pK_a + \log\left(\left[\frac{(F_1/P_1)_{low\ pH}}{(F_2/P_2)_{high\ pH}}\right] \frac{F_2/P_2 - \left[\frac{(F_2/P_2)_{low\ pH}}{(F_1/P_1)_{low\ pH}}\right] F_1/P_1}{F_1/P_1 - \left[\frac{(F_1/P_1)_{high\ pH}}{(F_2/P_2)_{high\ pH}}\right] F_2/P_2}\right).$$

where $pK_a \equiv -\log K_a$, "$K_a$" being the dissociation constant of the dye.

The partial pressure of carbon dioxide can be determined from absorbances and normalized fluorescent emissions measured for a dye solution containing a weakly acidic dye and $HCO_3^-$ as follows:

$$\frac{K_{a1}K_H}{K_a[HCO_3^-]}\left(\frac{(A_1)_{low\ pH}}{(A_2)_{high\ pH}}\right)P_{CO_2} = \frac{A_1 - \frac{(A_1)_{high\ pH}}{(A_2)_{high\ pH}} A_2}{A_2 - \frac{(A_2)_{low\ pH}}{(A_1)_{low\ pH}} A_1},$$

and:

$$\frac{K_{a1}K_H}{K_a[HCO_3^-]}\left[\frac{(F_1/P_1)_{low\ pH}}{(F_2/P_2)_{high\ pH}}\right]P_{CO_2} = \frac{F_1/P_1 - \left[\frac{(F_1/P_1)_{high\ pH}}{(F_2/P_2)_{high\ pH}}\right]F_2/P_2}{F_2/P_2 - \left[\frac{(F_2/P_2)_{low\ pH}}{(F_1/P_1)_{low\ pH}}\right]F_1/P_1}.$$

An especially preferred system for carrying out the invention includes an electronic controller comprising a programmed microprocessor in electrical communication with the light sources and the photodetector systems. Most preferably, the microprocessor is programmed to modulate the light sources; to accept signals representing intensity measurements from the photodetectors during time periods associated with the illumination of the dye by one or more wavelengths of light; and to process the intensity measurements in accordance with the complex ratiometric expressions given above. The preparation of a suitable program in accordance with the invention as disclosed herein is within the ordinary skill in the art and requires no undue experimentation.

Therefore, it is one object of the invention to provide methods and systems by which the analyte content of a medium can be determined to high resolution by exposing a dye solution to the analyte; measuring spectral properties of the dye corresponding to two wavelengths of light; and processing these spectral properties in accordance with a complex ratiometric expression. The invention will be further described in conjunction with the appended drawings and following detailed description.

DETAILED DESCRIPTION OF THE PREFERRED EMBODIMENT

Figure 1:
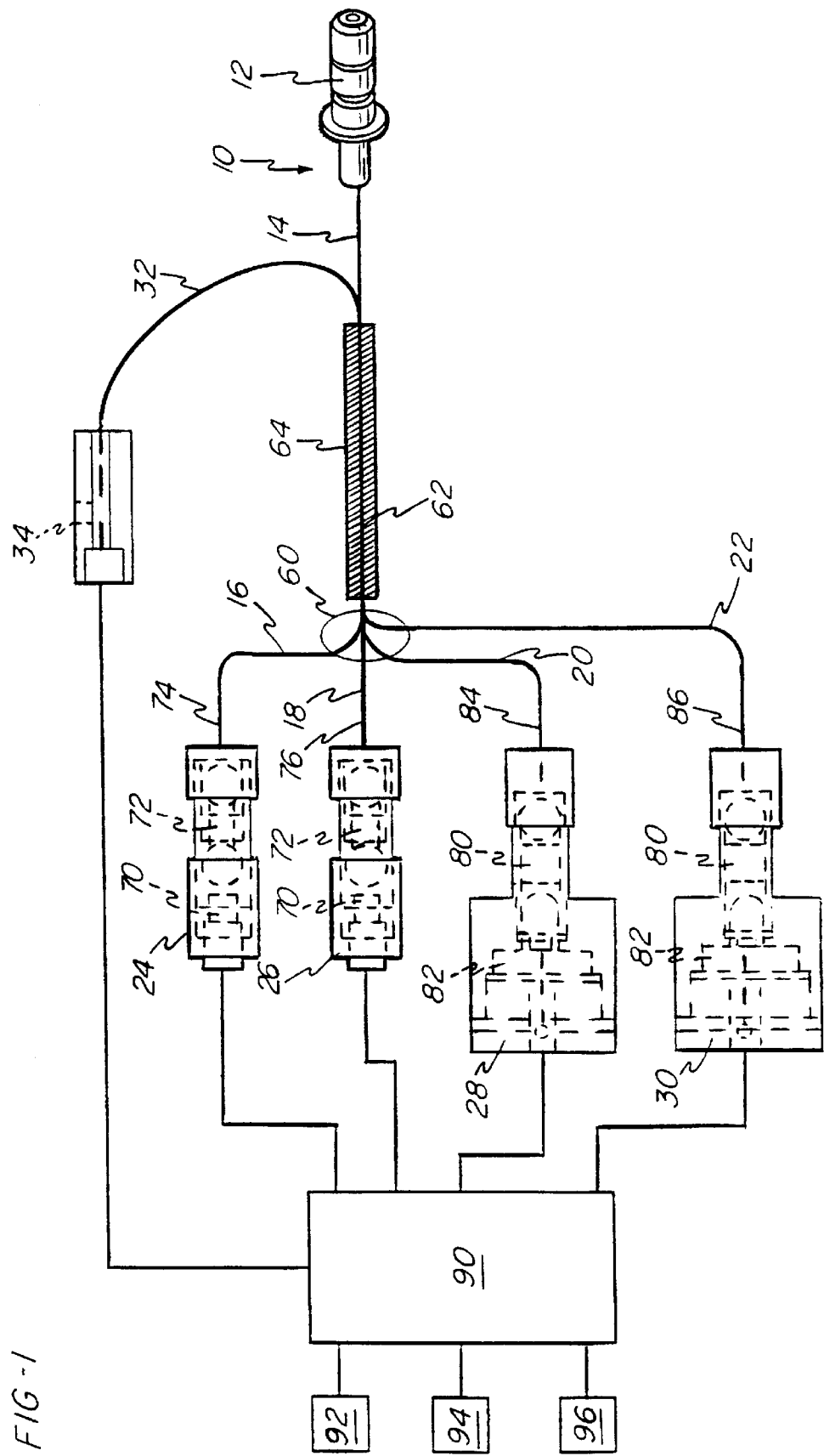
FIG. 1 is a schematic view of a first embodiment of an optical chemical sensor system in accordance with the invention.

As shown in FIG. 1, a first preferred embodiment of an optical chemical sensor system 10, capable of use for measuring analyte contents such as pH or the partial pressure of carbon dioxide, includes a sensor element or probe 12, a distal optical fiber 14, a first proximal optical fiber 16, a second proximal optical fiber 18, a third proximal optical fiber 20, a fourth proximal optical fiber 22, a first monochromatic light source 24, a second monochromatic light source 26, a first frequency-sensitive photodetector system 28, a second frequency-sensitive photodetector system 30, a bleed optical fiber 32 and a reference photodetector 34.

Figure 2:
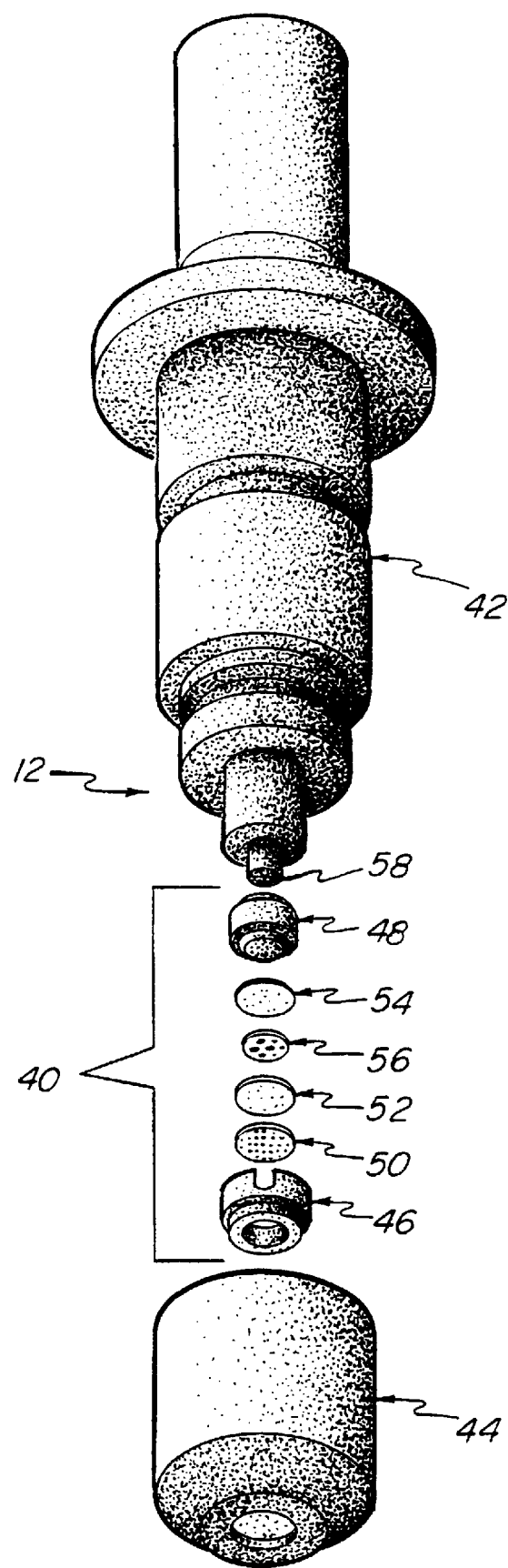
FIG. 2 is a schematic disassembled view of a preferred sensor element or probe for use in the optical chemical sensor system of FIG. 1.

As best shown in FIG. 2, an especially preferred probe 12 for use in the system 10 of FIG. 1 comprises a sensor capsule 40 housed between a sensor housing 42 and a sensor cap 44. The sensor capsule 40 includes an outer housing 46; an insert member 48; a perforated metal disc 50; a permeable polymeric membrane 52; and a light-transmissive, impermeable polymer membrane 54. The outer housing 46 and the insert member 48 snap together around the perforated disc 50 and the polymer membranes 52, 54 to form a unitary capsule 40 which may be easily removed and replaced without sacrificing the entire probe 12.

A pool or layer 56 of a fluid dye material is trapped in the preferred probe 12 between the polymer membranes 52, 54.

A distal end 58 of the distal optical fiber 14 (FIG. 1) extends through the sensor housing 42 into optical communication with the dye material 56 through the impermeable polymer membrane 54. The impermeable polymer membrane 54 separates and protects the distal end 58 of the distal optical fiber 14 (FIG. 1) from the dye material 56.

The preferred probe 12 is described in more detail in co-pending U.S. Provisional Patent Application No. 60/106,528, filed Oct. 31, 1998, the disclosure of which is incorporated herein by reference.

Returning to FIG. 1, the optical fibers 14, 16, 18, 20, 22 are each preferably formed of an amorphous, light transmissive material such as fused silicon, so as to channel the flow of light along their respective lengths. Distal end portions (collectively shown as 60) of the proximal optical fibers 16, 18, 20, 22 are fused to a proximal end portion 62 of the distal optical fiber 14 and encapsulated to form a fused coupling 64 with minimal impedance to the wavelengths of light at which the dye material 56 (FIG. 2) is to be illuminated and at which intensity measurements are to be taken.

The monochromatic light sources 24, 26 each comprise a light source 70, such as a bulb or a light emitting diode, and a band-pass filter 72 to isolate a wavelength at which the aqueous dye solution (not shown) is to be illuminated. The light sources 70 and the band-pass filters 72 are of conventional construction. The monochromatic light sources 24, 26 communicate with proximal end portions 74 and 76 of the first and second proximal optical fibers 16, 18 to permit the first and second proximal optical fibers 16, 18 to transmit monochromatic light from the monochromatic light sources 24, 26 toward the distal optical fiber 14.

The frequency-sensitive photodetector systems 28, 30 each include a band-pass filter 80 in optical communication with a measuring photodetector 82. The band-pass filters 80 and the measuring photodetectors 82 are of conventional construction. The band-pass filters 80 communicate with proximal end portions 84 and 86 of the third and fourth proximal optical fibers 20, 22. The frequency-sensitive photodetector systems 28, 30 each measure the intensity of a component of light returning through the third and fourth proximal optical fibers 20, 22 within a narrow range of wavelengths surrounding a selected wavelength.

The bleed optical fiber 32 is fused to the distal optical fiber 14 so that it directs a portion of the light propagating through the distal optical fiber 14 toward the reference photodetector 34. It preferably is formed of an amorphous, light transmissive material such as fused silicon and has a diameter much less than a diameter of the distal optical fiber 14 so that the portion of light directed through the bleed optical fiber 32 toward the reference photodetector 34 is much less than the portion directed through the distal optical fiber 14 toward the probe 12. This permits the reference photodetector 34 to monitor the intensity of light output by the two monochromatic light sources 24, 26 so as to provide a measure of the intensity of the light illuminating the dye material 56 (FIG. 2) in the probe 12.

Most preferably, the monochromatic light sources 24, 26; the frequency-sensitive photodetector systems 28, 30; and the reference photodetector 34 each communicate electronically with an electronic controller, such as a programmed microprocessor 90 having an arithmetic processor (not shown) and random-access memory (not shown). The controller modulates the light illuminating the dye material 56 (FIG. 2) in the probe 12, most preferably such that only one of the first and second monochromatic light sources 24, 26 illuminates the dye material 56 (FIG. 2) at any time. It also monitors signals received from the frequency-sensitive photodetector systems 28, 30 and the reference photodetector 34 to determine analyte content. In an especially preferred form, the microprocessor 90 communicates electronically with a readout such as a display 92, a printer 94 or a memory storage device 96 to report measurements performed by the system 10.

Systems having overall structure similar to that of the system 10 of FIG. 1 are described in more detail in co-pending U.S. Provisional Application, Ser. No. 60/122, 913, filed Mar. 5, 1999 in the name of Jamie N. Lussier, the disclosure of which is incorporated by reference.

In practice, the permeable polymer membrane 52 (FIG. 2) of the probe 12 is brought into contact with a medium of interest (not shown) so that molecular or ionic species (not shown) from the medium of interest diffuse through the perforated metal disc 50 (FIG. 2) and the permeable polymer membrane 52 (FIG. 2) to the layer of dye material 56 (FIG. 2). Meanwhile, the microprocessor 90 modulates the monochromatic light sources 24, 26 so that they alternately supply light at first and second illumination wavelengths, respectively. This light supplied by the two monochromatic light sources 24, 26 propagates through the first and second proximal optical fibers 16, 18; through the fused coupling 64; and through the distal optical fiber 14 toward the dye material 56 (FIG. 2) in the probe 12. A portion of the light supplied from the monochromatic light sources 24, 26 propagates through the bleed optical fiber 32 to enable the reference photodetector 34 to provide a measurement of the intensity of the illuminating light.

Output light from the probe 12 returns through the distal optical fiber 14, the fused coupling 64 and the third and fourth proximal optical fibers 20, 22 toward the frequency-sensitive photodetector systems 28, 30. The frequency-sensitive photodetector systems 28, 30 each measure the intensity of a narrow range of wavelengths of the light returning from the probe 12.

These measurements performed by the frequency-sensitive photodetector systems 28, 30, are communicated electronically to the microprocessor 90 in a conventional manner. An external analog-to-digital converter (not shown) may be provided to convert electrical signals (not shown) from the photodetector systems 28, 30 and the reference photodetector 24 into a form intelligible to the microprocessor 90.

The microprocessor 90 processes signals representing intensity measurements which it receives from the frequency-sensitive photodetector systems 28, 30 in order to determine the analyte content of the medium. More specifically, the microprocessor monitors signals from the frequency-sensitive photodetector systems 28, 30 during time periods associated with the illumination of the dye layer 56 (FIG. 2) by each of the monochromatic light sources 24, 26. The microprocessor 90 is further programmed to store these signals in variables associated with each of the wavelengths of illuminating light. These stored values are subsequently transferred to an arithmetic unit (not shown) of the microprocessor 90 to determine the analyte content by means of a complex ratiometric expression of the form:

$$Y_{analyte} = f([H^+]) = f\left(k_1 k_2 - \frac{X_1 - k_3 X_2}{X_2 - k_4 X_1}\right).$$

The preparation of a suitable program for the microprocessor 90 is within the ordinary skill in the art and requires no undue experimentation.

Figure 3:
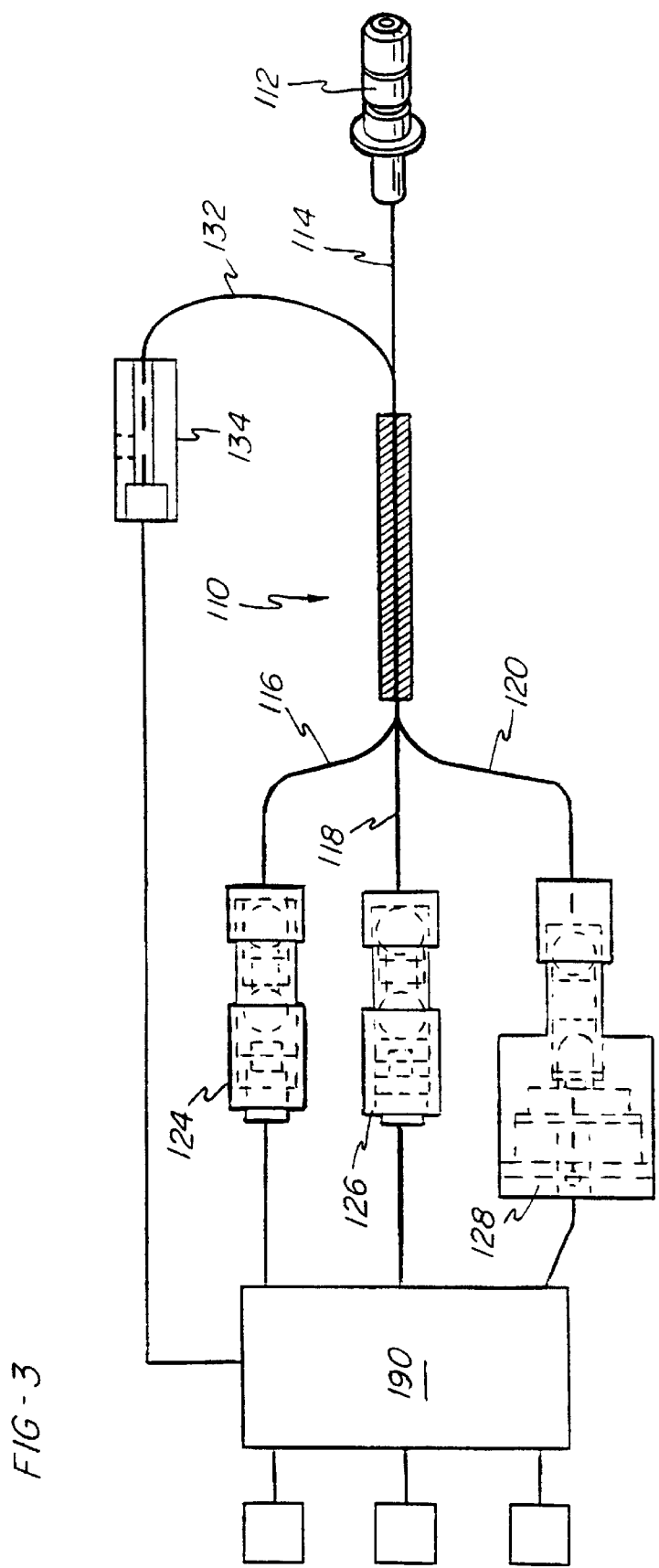
FIG. 3 is a schematic view of a second embodiment of an optical chemical sensor system in accordance with the invention.

As shown in FIG. 3, a second preferred embodiment of an optical chemical sensor system 110 includes a sensor element or probe 112, a distal optical fiber 114, a first proximal optical fiber 116, a second proximal optical fiber 118, a third proximal optical fiber 120, a first monochromatic light source 124, a second monochromatic light source 126, a frequency-sensitive photodetector system 128, a bleed optical fiber 132, a reference photodetector 134 and a controller including a microprocessor 190. The structure and operation of the system 110 is similar to that of the system 10 (FIG. 1), except that, in contrast to the system 10 (FIG. 1), only one wavelength returning from the probe 112 is measured.

One especially preferred dye solution 56 (FIG. 2) for use in the optical chemical sensor systems 10 of FIG. 1 and 110 of FIG. 3 is an aqueous solution containing HPTS. In the case of a system for measuring the partial pressure of carbon dioxide on a medium, a preferred dye solution 56 (FIG. 2) is an aqueous solution containing HPTS and an $HCO_3^-$ source, such as carbonic acid or a bicarbonate salt of an alkali metal.

Figure 4:
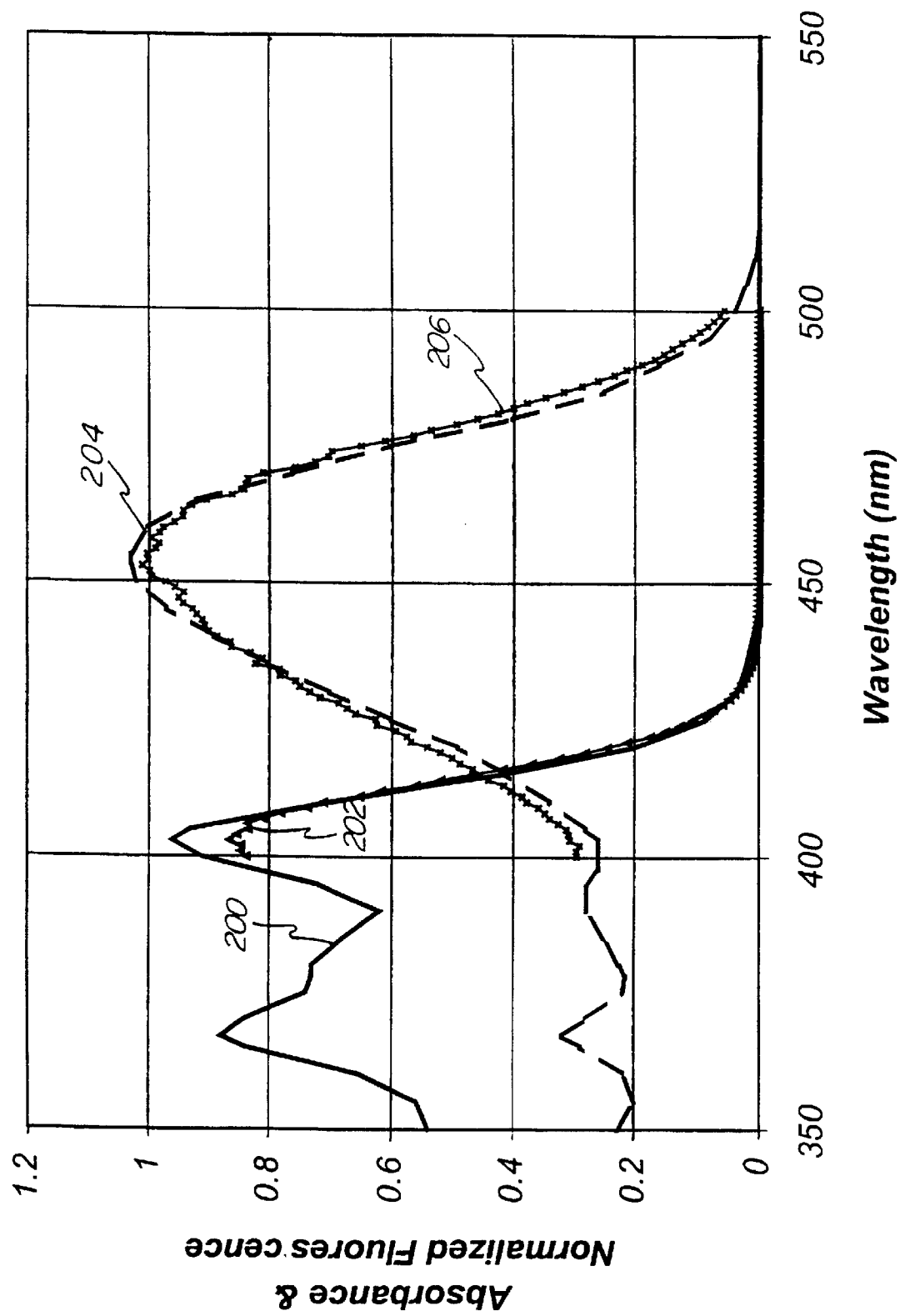
FIG. 4 is a graph showing the absorbance and excitation spectra of a dilute aqueous solution containing HPTS and $HCO_3^-$ at pH 3 and pH 12.

FIG. 4 is a graph showing absorption and excitation spectra for an aqueous dye solution comprising 50 $\mu$M HPTS, 0.1 mM $HCO_3^-$ and 0.5 M NaCl. Curves 200 and 202 represent the absorbance and excitation spectra, respectively, of the dye solution when exposed to a buffer solution having a pH of 3 (that is, a sufficiently low pH that only a negligible amount of the HPTS dissociates into $PTS^-$ conjugate base ion). Curves 204 and 206 represent the absorbance and excitation spectra, respectively, of the dye solution when exposed to a buffer solution having a pH of 12 (that is, a sufficiently high pH that all but a negligible amount of the HPTS dissociates into $PTS^-$ conjugate base ion).

As shown by curves 200 and 202, the undissociated HPTS molecules achieve peak absorbance at an illumination wavelength of approximately 403 nm and peak excitation at a wavelength of approximately 405 nm. As shown by curves 204 and 206, the $PTS^-$ conjugate base ions achieve peak absorbance at an illumination wavelength of approximately 454 nm and peak excitation at a wavelength of approximately 460 nm. When illuminated at their peak excitation wavelengths, both the undissociated HPTS molecules and the $PTS^-$ conjugate base ions fluoresce at approximately 515 nm. It will be noted that the undissociated HPTS molecules do not absorb substantial amounts of light at wavelengths above approximately 450 nm and consequently do not fluoresce significantly when illuminated by wavelengths above 450 nm.

In a system 10 (FIG. 1) for measuring the partial pressure of carbon dioxide by means of absorbance measurements using an aqueous dye solution comprising 50 $\mu$M HPTS, 0.1 mM $HCO_3^-$ and 0.5 M NaCl, the first and second illumination wavelengths are preferably 403 nm and 454 nm. These wavelengths correspond to peak absorbance wavelengths when the dye material is exposed to low and high pH buffer solutions, respectively.

Alternatively, in a system 110 (FIG. 3) for measuring the partial pressure of carbon dioxide using normalized fluorescent emission intensities using an aqueous dye solution comprising 50 $\mu$M HPTS, 0.1 mM $HCO_3^-$ and 0.5 M NaCl, the first and second illumination wavelengths are preferably 405 nm and 460 nm. These wavelengths correspond to peak excitation wavelengths when the dye material is exposed to low and high pH buffer solutions, respectively.

For such systems, the partial pressure of carbon dioxide may be determined as follows:

$$\frac{K_{a1}K_H}{K_a[\text{HCO}_3^-]} \frac{(A_{403\text{ nm}})_{\text{pH }3}}{(A_{454\text{ nm}})_{\text{pH }12}} P_{CO_2} = \frac{A_{403\text{ nm}} - \frac{(A_{403\text{ nm}})_{\text{pH }12}}{(A_{454\text{ nm}})_{\text{pH }12}} A_{454\text{ nm}}}{A_{454\text{ nm}} - \frac{(A_{454\text{ nm}})_{\text{pH }3}}{(A_{403\text{ nm}})_{\text{pH }3}} A_{403\text{ nm}}},$$

or, alternatively, $$\frac{K_{a1}K_H}{K_a[\text{HCO}_3^-]} \frac{(F_{405\text{ nm}}/P_{405\text{ nm}})_{\text{pH }3}}{(F_{460\text{ nm}}/P_{460\text{ nm}})_{\text{pH }12}} P_{CO_2} =$$

$$\frac{F_{405\text{ nm}}/P_{405\text{ nm}} - \left[\frac{(F_{405\text{ nm}}/P_{405\text{ nm}})_{\text{pH }12}}{(F_{460\text{ nm}}/P_{460\text{ nm}})_{\text{pH }12}}\right] F_{460\text{ nm}}/P_{460\text{ nm}}}{F_{460\text{ nm}}/P_{460\text{ nm}} - \left[\frac{(F_{460\text{ nm}}/P_{460\text{ nm}})_{\text{pH }3}}{(F_{405\text{ nm}}/P_{405\text{ nm}})_{\text{pH }3}}\right] F_{405\text{ nm}}/P_{405\text{ nm}}}.$$

(Note that the subscripts on the intensity measurements in the latter equation refer to the wavelengths at which the dye material is illuminated, not to the wavelengths at which the intensities are measured; in fact, both "$F_{405\text{ nm}}$" and "$F_{460\text{ nm}}$" are preferably measured at 515 nm.)

From the equations given above, it appears that the sensitivities of $CO_2$ partial pressure determinations performed in accordance with the invention are dependent on the magnitude of the ratio $(K_{a1}K_H)/(K_a[\text{HCO}_3^-])$. At 22° C., the Henry's Law constant for the preferred dye material is $K_H \approx 3.72 \times 10^{-4}$ M/% $CO_2$. For an aqueous dye solution comprising 50 μM HPTS, 0.1 mM $HCO_3^-$ and 0.5 M NaCl, the ratio $K_{a1}/K_1 \approx 4.57$ near room temperature. Under these conditions, the coefficient:

$$\frac{K_{a1}K_H}{K_a} \approx 1.63 \times 10^{-3} \frac{M}{\% \text{ CO}_2}.$$

In the case of a system 10 (FIG. 1), 110 (FIG. 3) for detecting pH by means of performing absorbance or normalized fluorescent emission intensity measurements on a dilute aqueous dye solution comprising HPTS alone or in combination with NaCl, pH may be determined by expressions of the form:

$$\text{pH} = pK_a + \log\left(\left[\frac{(A_{403\text{ nm}})_{\text{pH }3}}{(A_{454\text{ nm}})_{\text{pH }12}}\right] \frac{A_{454\text{ nm}} - \frac{(A_{454\text{ nm}})_{\text{pH }3}}{(A_{403\text{ nm}})_{\text{pH }3}} A_{403\text{ nm}}}{A_{403\text{ nm}} - \frac{(A_{403\text{ nm}})_{\text{pH }12}}{(A_{454\text{ nm}})_{\text{pH }12}} A_{454\text{ nm}}}\right),$$

and:

$$\text{pH} = pK_a + \log\left(\left[\frac{(F_{405\text{ nm}}/P_{405\text{ nm}})_{\text{pH }3}}{(F_{460\text{ nm}}/P_{460\text{ nm}})_{\text{pH }12}}\right] F_{460\text{ nm}}/P_{460\text{ nm}} -\right.$$

$$\left.\frac{\left[\frac{(F_{460\text{ nm}}/P_{460\text{ nm}})_{\text{pH }3}}{(F_{405\text{ nm}}/P_{405\text{ nm}})_{\text{pH }3}}\right] F_{405\text{ nm}}/P_{405\text{ nm}}}{F_{405\text{ nm}}/P_{405\text{ nm}} - \left[\frac{(F_{405\text{ nm}}/P_{405\text{ nm}})_{\text{pH }12}}{(F_{460\text{ nm}}/P_{460\text{ nm}})_{\text{pH }12}}\right] F_{460\text{ nm}}/P_{460\text{ nm}}}\right)$$

where $pK_a \equiv -\log K_a$, "$K_a$" being the dissociation constant of the dye.

As suggested in FIG. 4, the undissociated HPTS molecules do not absorb substantial amounts of light at wavelengths above approximately 450 nm. Therefore, $(A_{454\text{ nm}})_{pH3}$ and $(F_{460\text{ nm}})_{pH3}$ are each nearly zero.

In the case of a system 10 (FIG. 1), 110 (FIG. 3) for detecting pH using a dilute aqueous dye solution comprising HPTS alone or in combination with NaCl, this observation suggests that the relationships between ratios of the measured absorbances or normalized fluorescent emission intensities, on the one hand, and the pH, on the other, reduce to the form:

$$\text{pH} = pK_a + \log\left(\frac{\frac{(A_{403\text{ nm}})_{\text{pH }3}}{(A_{454\text{ nm}})_{\text{pH }12}} A_{454\text{ nm}}}{A_{403\text{ nm}} - \frac{(A_{403\text{ nm}})_{\text{pH }12}}{(A_{454\text{ nm}})_{\text{pH }12}} A_{454\text{ nm}}}\right),$$

and:

$$\text{pH} =$$

$$pK_a + \log\left(\frac{\frac{(F_{405\text{ nm}}/P_{405\text{ nm}})_{\text{pH }3}}{(F_{460\text{ nm}}/P_{460\text{ nm}})_{\text{pH }12}} F_{460\text{ nm}}/P_{460\text{ nm}}}{F_{405\text{ nm}}/P_{405\text{ nm}} - \left[\frac{(F_{405\text{ nm}}/P_{405\text{ nm}})_{\text{pH }12}}{(F_{460\text{ nm}}/P_{460\text{ nm}})_{\text{pH }12}}\right] F_{460\text{ nm}}/P_{460\text{ nm}}}\right).$$

In the case of a system 10 (FIG. 1), 110 (FIG. 3) for detecting the partial pressure of carbon dioxide, the observation that $(A_{454\text{ nm}})_{pH3} \approx 0$ and $(F_{460\text{ nm}})_{pH3} = 0$ suggests that the relationships between ratios of the measured absorbances or normalized fluorescent emission intensities, on the one hand, and the partial pressure of carbon dioxide, on the other, might reduce to linear form:

$$\frac{K_{a1}K_H}{K_a[\text{HCO}_3^-]} \left(\frac{(A_{403\text{ nm}})_{\text{pH }3}}{(A_{454\text{ nm}})_{\text{pH }12}}\right) P_{CO_2} = \left[\frac{A_{403\text{ nm}}}{A_{454\text{ nm}}} - \frac{(A_{403\text{ nm}})_{\text{pH }3}}{(A_{454\text{ nm}})_{\text{pH }12}}\right],$$

or, alternatively:

$$\frac{K_{a1}K_H}{K_a[\text{HCO}_3^-]} \frac{(F_{405\text{ nm}}/P_{405\text{ nm}})_{\text{pH }3}}{(F_{460\text{ nm}}/P_{460\text{ nm}})_{\text{pH }12}} P_{CO_2} =$$

$$\left[\frac{F_{405\text{ nm}}/P_{405\text{ nm}}}{F_{460\text{ nm}}/P_{460\text{ nm}}} - \frac{(F_{405\text{ nm}}/P_{405\text{ nm}})_{\text{pH }12}}{(F_{460\text{ nm}}/P_{460\text{ nm}})_{\text{pH }12}}\right].$$

Depending on the optical system and alignment, however, this simple linear expression could lead to undesirable errors in measurements even though the residual fluorescence of the undissociated HPTS molecules at wavelengths above 450 nm is insignificant.

Figure 5:
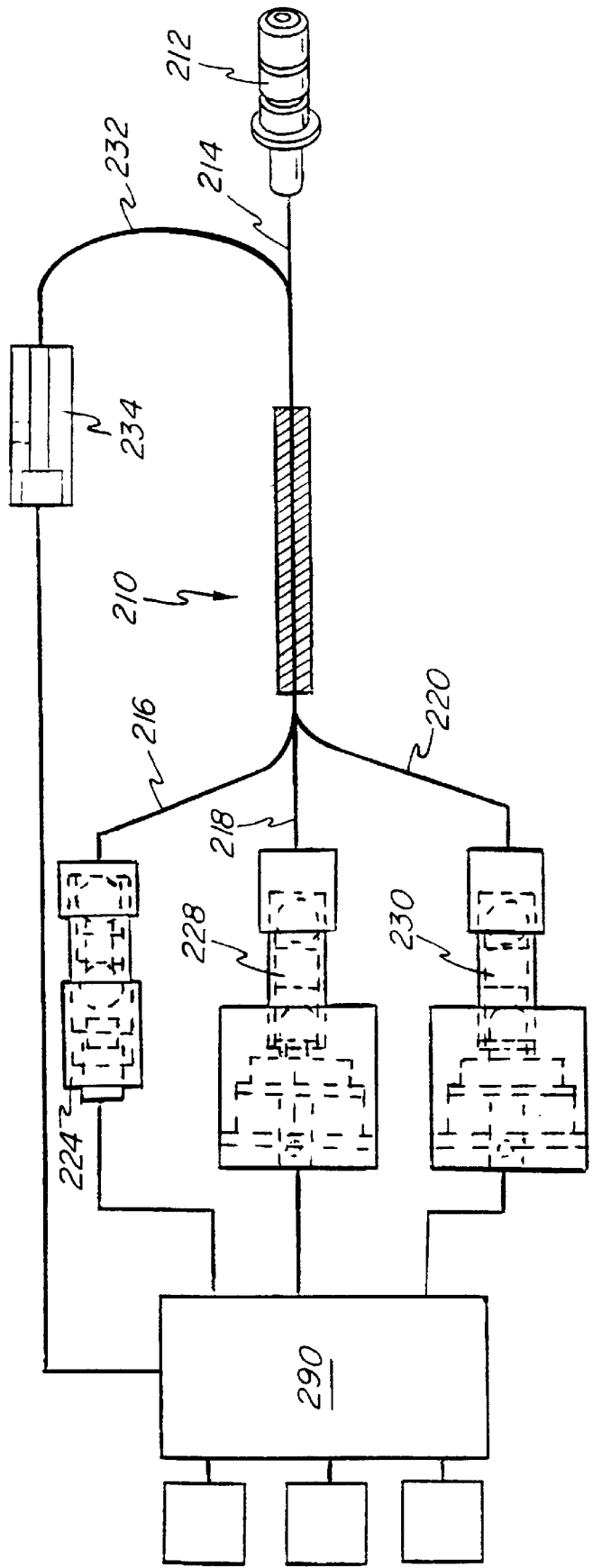
FIG. 5 is a schematic view of a third embodiment of an optical chemical sensor system in accordance with the invention.

As shown in FIG. 5, a third preferred embodiment of an optical chemical sensor system 210 includes a sensor element or probe 212, a distal optical fiber 214, a first proximal optical fiber 216, a second proximal optical fiber 218, a third proximal optical fiber 220, a monochromatic light source 224, a first frequency-sensitive photodetector system 228, a second frequency-sensitive photodetector system 230, a bleed optical fiber 232, a reference photodetector 234 and a controller including a microprocessor 290. The structure and operation of the system 210 is similar to that of the systems 10 (FIG. 1), 110 (FIG. 3), except that, in contrast to the system 10 (FIG. 1), the single monochromatic light source 224 illuminates the dye material 56 (FIG. 2) at only one wavelength of light. In accordance with an especially preferred embodiment, the monochromatic light source 224 remains lit whenever measurements are being taken and the microprocessor 290 alternately accepts signals representative of intensity measurements from the first and second frequency-sensitive photodetector systems 228, 230.

In the case of a system for measuring pH, another preferred dye material 56 (FIG. 2) for use in the optical chemical sensor system 10 (FIG. 1), 210 (FIG. 5) is an aqueous solution including c-SNAFL. In the case of a system for measuring the partial pressure of carbon dioxide on a medium, a preferred dye material 56 (FIG. 2) is an aqueous solution including c-SNAFL and an $HCO_3^-$ source, such as carbonic acid or a bicarbonate salt of an alkali metal.

Figure 6:
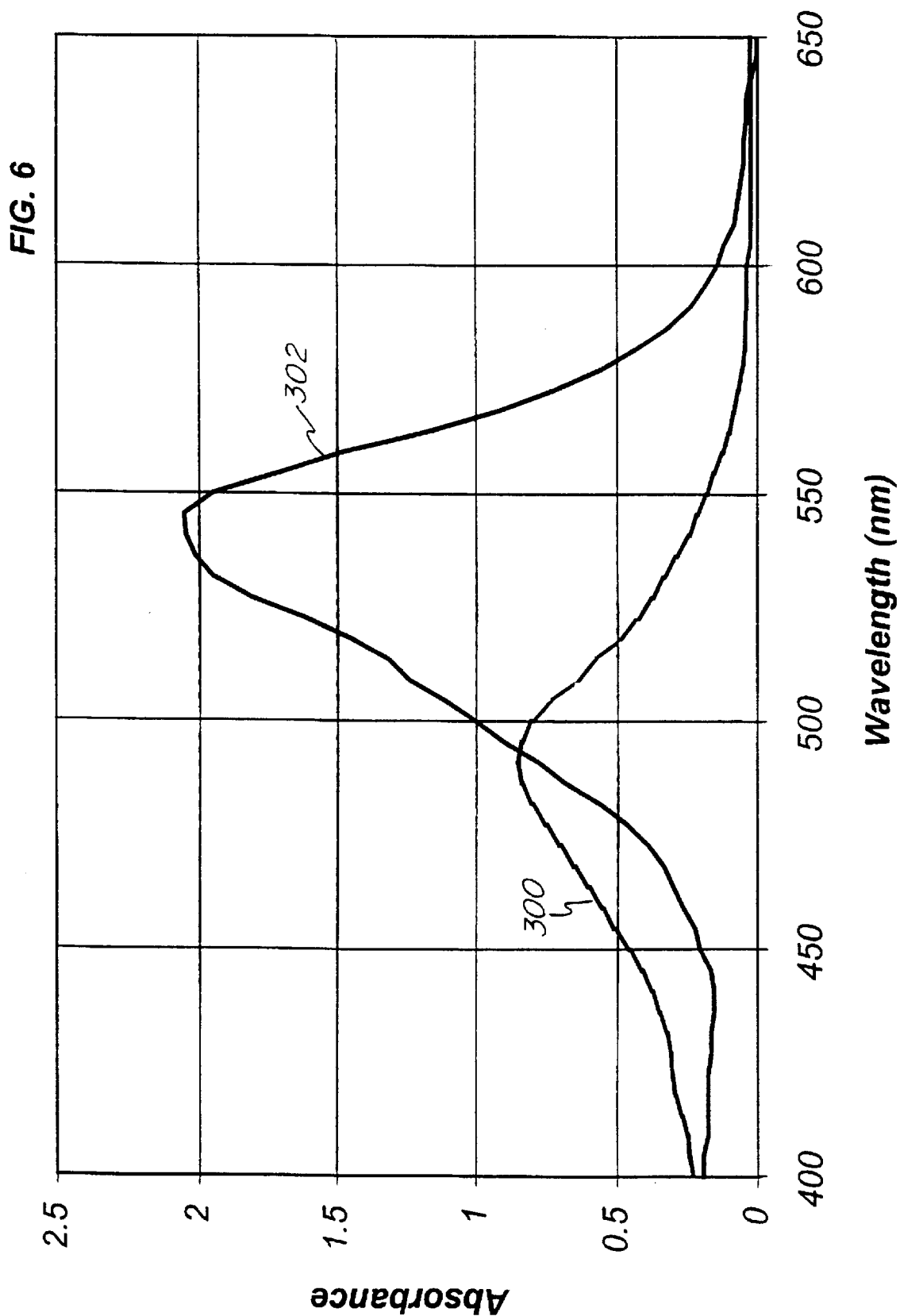
FIG. 6 is a graph showing the absorbance spectra of a dilute aqueous solution containing c-SNAFL and $HCO_3^-$ at pH 1.71 and pH 11.46.

FIG. 6 is a graph showing absorption spectra for an aqueous dye solution comprising 46.9 µM c-SNAFL, 3 mM $HCO_3^-$ and 0.5 M NaCl. Curve 300 represents the absorbance spectrum of the dye solution when exposed to a buffer solution having a pH of 1.71 (that is, a sufficiently low pH that only a negligible amount of the c-SNAFL dissociates into its conjugate base ion). Curve 302 represents the absorbance spectrum of the dye solution when exposed to a buffer solution having a pH of 11.46 (that is, a sufficiently high pH that all but a negligible amount of the c-SNAFL dissociates into its conjugate base ion).

Curve 300 indicates that the undissociated c-SNAFL molecules achieve peak absorbance at an illumination wavelength of approximately 490 nm. Curve 302 indicates that the conjugate base ions achieve peak absorbance at an illumination wavelength of approximately 540 nm.

Figure 7:
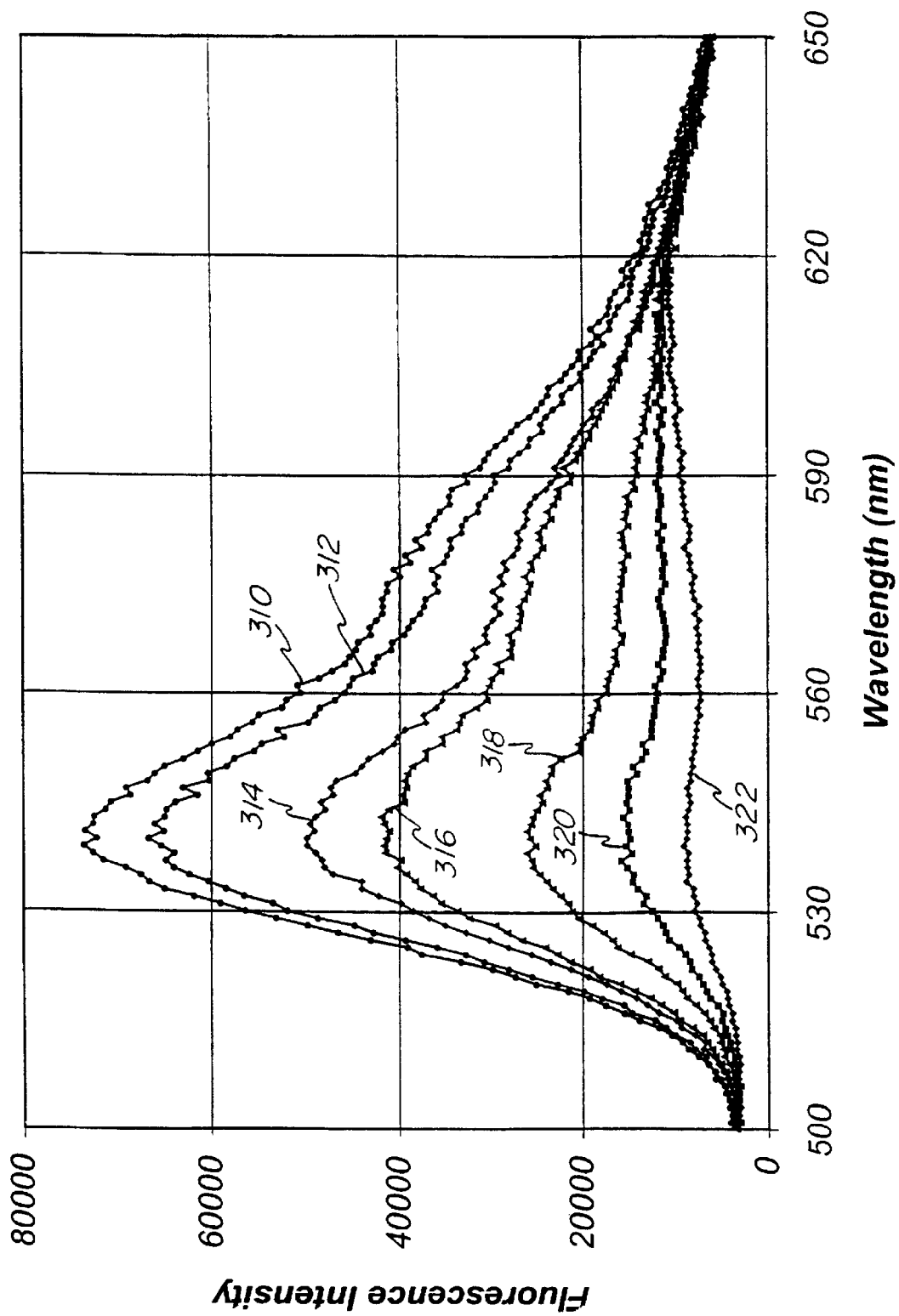
FIG. 7 is a graph showing the fluorescent emission spectra of a dilute aqueous solution containing c-SNAFL and $HCO_3^-$ at several pH values between pH 7 and pH 9 after being excited at 480 nm.

FIG. 7 is a graph showing fluorescent emission spectra for an aqueous dye solution comprising 15.63 µM c-SNAFL, 1 mM $HCO_3^-$ and 0.167 M NaCl exposed to buffer solutions having pH values in a range of pH values between pH 7 and pH 9 after excitation at 480 nm. More specifically, these curves show fluorescence emission spectra for dye solutions exposed to buffer solutions having the following pH values:

| | |
|---|---|
| Curve 310 | pH 7.38 |
| Curve 312 | pH 7.53 |
| Curve 314 | pH 7.71 |
| Curve 316 | pH 7.88 |
| Curve 318 | pH 8.29 |
| Curve 320 | pH 8.64 |
| Curve 322 | pH 9 |

It will be noted that each of these curves reaches a local maximum at approximately 540 nm. The curves generated at higher pH values, and particularly the curve 322 corresponding to pH 9, begin to show a local maximum which shifts toward 630 nm with increasing pH.

In a system 10 (FIG. 1) for measuring the partial pressure of carbon dioxide using absorbance measurements performed on an aqueous dye solution including c-SNAFL, an $HCO_3^-$ source and sodium chloride, the first and second illumination wavelengths are preferably 490 nm and 540 um, respectively. These wavelengths correspond to peak absorbance wavelengths when the dye material is exposed to low and high pH buffer solutions, respectively.

Alternatively, in a system 210 (FIG. 5) for measuring the partial pressure of carbon dioxide using fluorescent emission intensity measurements performed on an aqueous dye solution comprising c-SNAFL, an $HCO_3^-$ source and sodium chloride, the dye material is preferably illuminated at a wavelength of 480 nm. The fluorescent emissions are preferably measured at wavelengths of 540 nm and 630 nm. These wavelengths correspond to peak fluorescent emission wavelengths when the dye material is exposed to low and high pH buffer solutions, respectively, and illuminated at 480 nm.

Since the system 210 (FIG. 5) uses a single monochromatic light source 224 to illuminate the dye material 56 (FIG. 2) to measure normalized fluorescent emission intensity at both 540 nm and 630 nm, the same illumination intensity would be used for normalizing the raw fluorescent intensity measurements at each wavelength. Therefore, the ratio of any two normalized fluorescent emission intensities equals the ratio of the corresponding raw fluorescent emission intensity measurements.

For such systems, the partial pressure of carbon dioxide may be determined as follows:

$$\frac{K_{a1}K_H}{K_a[HCO_3^-]} \frac{(A_{490nm})_{pH\,2}}{(A_{540nm})_{pH\,12}} P_{CO_2} = \frac{A_{490nm} - \frac{(A_{490nm})_{pH\,12}}{(A_{540nm})_{pH\,12}} A_{540nm}}{A_{540nm} - \frac{(A_{540nm})_{pH\,2}}{(A_{490nm})_{pH\,2}} A_{490nm}},$$

or, alternatively, $$\frac{K_{a1}K_H}{K_a[HCO_3^-]} \left[\frac{(F_{540nm})_{pH\,5.5}}{(F_{630nm})_{pH\,12}}\right] P_{CO_2} = \frac{F_{540nm} - \left[\frac{(F_{540nm})_{pH\,12}}{(F_{630nm})_{pH\,12}}\right] F_{630nm}}{F_{630nm} - \left[\frac{(F_{630nm})_{pH\,5.5}}{(F_{540nm})_{pH\,5.5}}\right] F_{540nm}},$$

(Note that the subscripts on the intensity measurements in the latter equation refer to the wavelengths at which the intensities are measured, not the wavelengths at which the dye material is illuminated.)

For an aqueous dye solution containing c-SNAFL, $HCO_3^-$ and NaCl, the ratio $K_{a1}/K_a \approx 22.9$ near room temperature. Under these conditions, the sensitivity coefficient:

$$\frac{K_{a1}K_H}{K_a} \approx 8.62 \times 10^{-3} \frac{M}{\% \, CO_2}.$$

Note that, in both dye systems, the shorter wavelength of the two preferably corresponds with the undissociated acid while the longer wavelength preferably corresponds with the conjugate base. Thus, when the method of the present invention uses an expression of the form:

$$\frac{K_{a1}K_H}{K_a[HCO_3^-]} \left[\frac{(F_1/P_1)_{low\,pH}}{(F_2/P_2)_{high\,pH}}\right] P_{CO_2} = \frac{F_1/P_1 - \left[\frac{(F_1/P_1)_{high\,pH}}{(F_2/P_2)_{high\,pH}}\right] F_2/P_2}{F_2/P_2 - \left[\frac{(F_2/P_2)_{low\,pH}}{(F_1/P_1)_{low\,pH}}\right] F_1/P_1}$$

to process normalized fluorescent emission intensity measurements performed on an aqueous solution of a weakly acidic dye, the constant "$k_3$" is preferably the ratio of the normalized fluorescent emission intensities of the conjugate base (that is, of intensity measurements taken while the dye material is exposed to a buffer solution of high pH) corresponding to the shorter and longer wavelengths, respectively. The constant "$k_4$" is preferably the ratio of the fluorescent emission intensities of the undissociated acid (that is, of intensity measurements taken while the dye material is exposed to a buffer solution of low pH) corresponding to the longer and shorter wavelengths, respectively.

Thus, $k_3$ preferably represents the residual fluorescence of the conjugate base at the shorter wavelength when the dye exists in the pure acid form. Similarly, $k_4$ preferably represents the residual fluorescence of the undissociated acid at the longer wavelength. These two residual fluorescence signals are being subtracted off proportionally from the relevant fluorescence in the numerator and the denominator of the complex ratio.

On the other hand, the constant "$k_2$" is preferably the ratio of the fluorescence of the undissociated acid and conjugate base at their corresponding wavelengths. For the HPTS dye, the ideal situation would be to have the same amount of excitation power or the same ratio of excitation powers going into the optical fiber through the fiber coupler for all optical instruments. For the SNAFL dye, the similar ideal situation would be to have the same ratio of the emissions corresponding to wavelengths of 540 nm and 630 nm (under the condition of same $CO_2$ partial pressure) for all optical instruments. This would require the coupling optics at the fiber coupler to be aligned and coupled into the fiber in the same way for all optical instruments for the HPTS dye. Similarly, the c-SNAFL dye system would require that the ratio of the fluorescent emissions corresponding to 540 nm and 630 nm be the same for all optical instruments.

Due to imperfections in the optics coupling the light sources and the frequency-sensitive photodetector systems with the sensor probe, the actual ratios of the excitation powers coupled into the fiber for the HPTS dye will vary. Similarly, variations at the band-pass filters for the c-SNAFL dye will lead to variations in the ratios of the fluorescent emission intensities. To harmonize these differences, and to lower the demand on optical alignment and adjustment of the same ratio of excitation powers to the fiber for all optical instruments, it is necessary to calibrate the instrument using buffer solutions of high and low pH. This instrument calibration procedure will normalize, using the two boundary solutions, the varying excitation power ratio due to the inconsistent coupling of the 405 nm and 460 nm excitation powers to the fiber through the fiber coupler for the HPTS dye (double excitation/single emission), and the variations of the 540 nm and 630 nm emissions due to variable band-pass filters for the SNAFL dye (single excitation/double emission).

Once the different constants $k_1$–$k_4$ are calculated, they are preferably stored in the microprocessor 90 as the factory calibration constants for the instrument. In a less-than-ideal situation, the $CO_2$ sensor probe 12 (FIG. 1), 112 (FIG. 3), 212 (FIG. 5) is expected to give the same reading for different optical instruments because all optical instruments have been calibrated and normalized through the constants $k_1$–$k_4$.

It has been found that systems 10 (FIG. 1), 210 (FIG. 5) using dye solutions including c-SNAFL tend to be more sensitive to small changes in the partial pressure of carbon dioxide than systems 10 (FIG. 1), 110 (FIG. 3) using HPTS. The sensitivity coefficients of a sensor system using an aqueous dye solution containing 50 $\mu$M HPTS, 1 mM $HCO_3^-$ and 0.5 M NaCl were measured at room temperature and found to be approximately:

$$\frac{K_{a1}K_H}{K_a[HCO_3^-]}\left(\frac{(A_{403nm})_{pH\,3}}{(A_{454nm})_{pH\,12}}\right) \approx 0.000204 \text{ 1/ppm } CO_2$$

for the absorbance case and:

$$\frac{K_{a1}K_H}{K_a[HCO_3^-]} \frac{(F_{405nm}/P_{405nm})_{pH\,3}}{(A_{460nm}/P_{460nm})_{pH\,12}} \approx 0.000126 \text{ 1/ppm } CO_2$$

for the fluorescence case. The sensitivity coefficients of a sensor system using an aqueous dye solution containing 15.6 $\mu$M HPTS, 1 mM $HCO_3^-$ and 0.167 M NaCl were measured at room temperature and found to be approximately:

$$\frac{K_{a1}K_H}{K_a[HCO_3^-]} \frac{(A_{490nm})_{low\,pH}}{(A_{540nm})_{pH\,12}} \approx 0.0008 \text{ 1/ppm } CO_2$$

for the absorbance case and:

$$\frac{K_{a1}K_H}{K_a[HCO_3^-]}\left[\frac{(F_{540nm})_{low\,pH}}{(F_{630nm})_{pH\,12}}\right] \approx 0.001196 \text{ 1/ppm } CO_2$$

for the absorbance case.

For this reason, systems using dye solutions including c-SNAFL are preferred for oceanographic measurements, where small differences in the partial pressure of carbon dioxide must be resolved. Systems using dye solutions including HPTS are preferred in some biotechnology applications where higher dissolved carbon dioxide ranges are anticipated. The sensitivity of the sensor system can be optimized by adjusting the concentration of $HCO_3^-$ in the dye solution, but at the risk of lowering the upper bound of the range of carbon dioxide partial pressures which the sensor system is capable of accurately measuring.

Three factors likely to affect the performance of a system 10 (FIG. 1), 110 (FIG. 3), 210 (FIG. 5), in which spectral measurements performed on an aqueous dye solution are used to measure the $CO_2$ partial pressure on an aqueous medium, include the nature of the material comprising the membrane 52 (FIG. 2), the volume of the dye layer 56 (FIG. 2) and the osmolarity of the dye solution.

Preferred materials for the membrane 52 (FIG. 2) include 10 $\mu$m polytetrafluoroethylene [hereinafter "PTFE"] and 127 $\mu$m silicone rubber. The preferred silicone rubber membrane is believed to have a $CO_2$ permeability of $2400 \times 10^{-13}$ cm$^2$/sec, which is approximately 320 times higher than the permeability of the preferred PTFE membrane, which is believed to be $7.5 \times 10^{-13}$ cm$^2$/sec. Since the $CO_2$ permeability of the preferred silicone rubber material is about four orders of magnitude larger than that of the preferred PTFE material, it would be expected that a sensor system using a silicone rubber membrane will respond much faster than a system using a PTFE membrane of the same thickness. While this expectation has been borne out experimentally, the difference in the response times is narrowed by the greater thickness of the preferred silicone rubber membrane as opposed to that of the preferred PTFE membrane.

Another advantage of silicone rubber is that it inhibits the diffusion of dissolved hydrogen ion from the medium into the dye solution. This improves the correspondence between the partial pressure of carbon dioxide in the medium and the pH in the vicinity of the dye solution.

On the other hand, the water permeability of the preferred silicone rubber is believed to be $3200 \times 10^{-13}$ cm$^2$/sec, while the preferred PTFE is believed to have a water permeability of only $1 \times 10^{-13}$ cm$^2$/sec. As a result, the silicone rubber may be at a disadvantage in maintaining the water vapor inside the sensor capsule 40 (FIG. 2) when there is a change of osmolarity outside the capsule 40.

The response time of the system increases with the volume of the dye layer 56 (FIG. 2) due to the additional time required for the dye solution to reach equilibrium. On the other hand, increasing the volume of the dye layer 56 also improves the long term stability of the sensor capsule 40, in that more time likely will be required to bleach the larger volume of dye.

The osmolarity of the dye solution also affects the long term stability of the sensor system. Where the osmolarity of an aqueous dye solution differs significantly from that of an aqueous medium of interest, osmotic pressure will tend to cause water vapor to move between the dye layer 56 (FIG. 2) and the medium. A change in the aqueous content of the dye layer 56 will tend to change the concentration of the dye and of the $HCO_3^-$ in the buffer solution, thereby altering the relationship between the spectral properties of the dye solution and the partial pressure of carbon dioxide on the medium.

In the case of oceanographic sensors, the osmolarity of the dye solution may be adjusted by adding NaCl or another salt to approximate the osmolarity of sea water. The selection of the nature and amount of such agents to adjust the osmolarity of the dye solution is within the ordinary skill in the art.

The following examples and comparative examples are illustrative only and it is not intended that the invention be restricted thereto.

EXAMPLE 1

The relationships between pH values and the spectral properties of a series of aqueous dye solutions containing HPTS were studied experimentally. Dye solutions containing 50 $\mu$M HPTS, 10 mM $HCO_3^-$ and 0.5 M NaCl were mixed with small amounts of HCl and NaOH buffer solutions to prepare mixtures having a range of known pH values between about pH 5 and pH 9. The absorbances of these mixtures were measured at illumination wavelengths of 405 nm and 453 nm. These absorbances were processed and compared to the known pH values of the mixtures.

Figure 8:
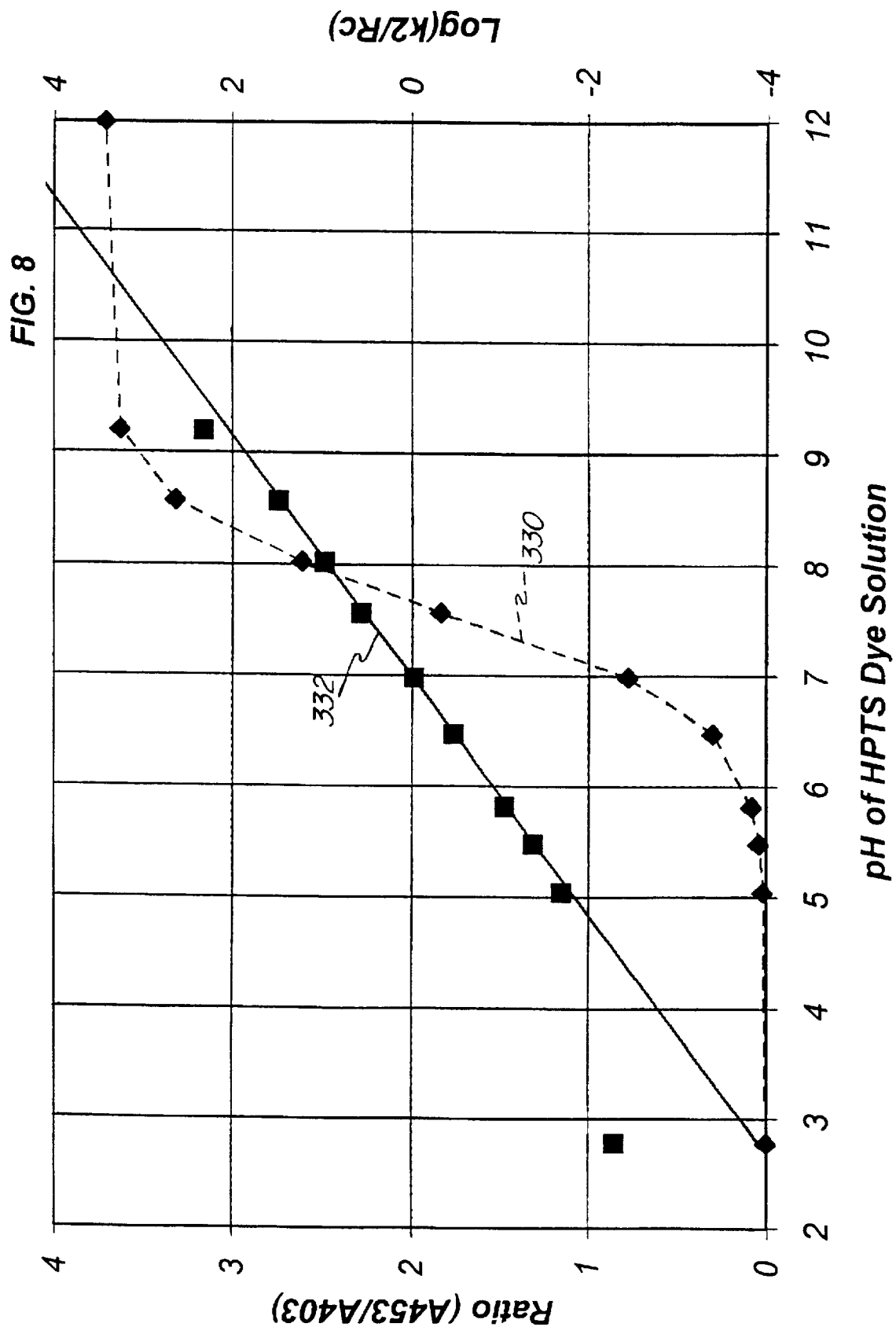
FIG. 8 is a graph comparing simple and complex ratios of measured absorbances of aqueous dye solutions having the composition 50 $\mu$M HPTS+10 mM $HCO_3^-$+0.5 M NaCl, each buffered to a different pH value, with the pH values of the solutions.

The results of these measurements are plotted in FIG. 8. Curve 330 in FIG. 8 shows the relationship between the simple ratios $A_{453\,nm}/A_{405\,nm}$ measured for each solution and the known pH values of the solutions. Curve 332 shows the relationship between the quantities $\log(k_2/R_c)$, where $k_2=(A_{403\,nm})_{pH\,3}/(A_{453\,nm})_{pH\,12}$ and the complex ratio "$R_c$" is defined by the expression:

$$\frac{A_{403nm} - \frac{(A_{403nm})_{pH\,12}}{(A_{453nm})_{pH\,12}} A_{453nm}}{A_{453nm} - \frac{(A_{453nm})_{pH\,3}}{(A_{403nm})_{pH\,3}} A_{403nm}}$$

measured for each solution and the pH values of the solutions. It will be noted that a strong linear correlation exists between the common logarithms of the quantities $\log(k_2/R_c)$ and the known pH values over the four order of magnitude of hydrogen ion concentration studied, whereas the relationship between the simple ratios and the pH values is visibly non-linear.

The strong linear correlation between the common logarithms of the complex ratios and the pH values over the range from pH 5 to pH 9 was confirmed statistically. It was found that the line 332 of FIG. 8 had a slope of 1.08 and that the correlation between the line 332 and the data points had a square deviation of $R^2=0.9998$. This strong correlation indicates that the common logarithm of the complex ratio of the absorbances provides an accurate measure of the pH in the vicinity of the dye solution.

EXAMPLE 2

The relationships between pH values and the spectral properties of a series of aqueous dye solutions containing c-SNAFL were studied experimentally. Dye solutions containing 11.7 $\mu$M c-SNAFL, 0.2 mM $HCO_3^-$ and 0.24 M NaCl were mixed with small amounts of HCl and NaOH buffer solutions to prepare mixtures having a range of known pH values between about pH 7 and pH 11. These mixtures were illuminated at a wavelength of 480 nm. The fluorescent emission intensities of these mixtures were measured at wavelengths of 540 nm and 630 nm. These fluorescent emission intensities were processed and compared to the known pH values of the mixtures.

Figure 9:
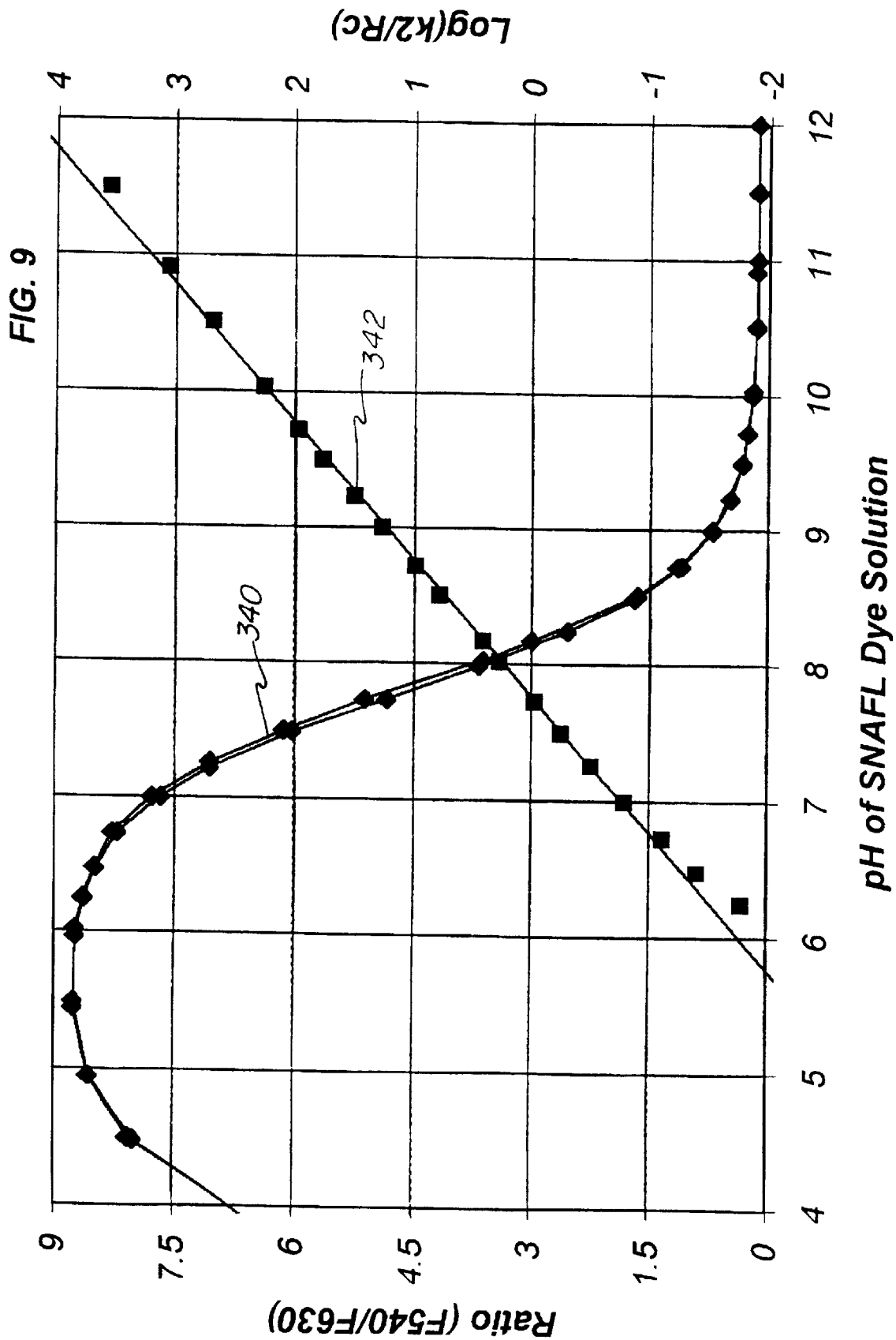
FIG. 9 is a graph comparing simple and complex ratios of measured fluorescent emissions from aqueous dye solutions having the compositions 11.7 $\mu$M c-SNAFL+0.2 mM $HCO_3^-$+0.24 M NaCl, each buffered to a different pH value, with the pH values of the solutions.

The results of these measurements are plotted in FIG. 9. The curve 340 in FIG. 9 shows the relationship between the simple ratios $F_{540\,nm}/F_{630\,nm}$ measured for each solution and the known pH values of the solutions. The curve 342 shows the relationship between the quantities $\log(k_2/R_c)$, where $k_2=(F_{540\,nm})_{pH\,5.5}/(F_{630\,nm})_{pH\,12}$ and the complex ratio "$R_c$" is defined by the expression:

$$\frac{F_{540nm} - \frac{(F_{540nm})_{pH\,12}}{(F_{630nm})_{pH\,12}} F_{630nm}}{F_{630nm} - \frac{(F_{630nm})_{pH\,5.5}}{(F_{540nm})_{pH\,5.5}} F_{540nm}}$$

measured for each solution and the pH values of the solutions. It will be noted that a strong linear correlation exists between the common logarithms of the quantities $\log(k_2/R_c)$ and the known pH values over the four order of magnitude of hydrogen ion concentration studied, whereas the relationship between the simple ratios and the pH values is visibly non-linear.

The strong linear correlation between the common logarithms of the complex ratios and the pH values over the range from pH 7 to pH 11 was confirmed statistically. It was found that the line 342 of FIG. 8 had a slope of 1.009 and that the correlation between the line 342 and the data points had a square deviation of $R^2=0.9995$. This strong correlation indicates that the common logarithm of the complex ratio of the fluorescent emission intensities provides an accurate measure of the pH in the vicinity of the dye solution.

EXAMPLE 3

Carbon dioxide gas was bubbled into a first batch of aqueous dye solutions containing 15.6 $\mu$M c-SNAFL, 1 mM $HCO_3^-$ and 0.167 M NaCl and a second batch of aqueous dye solutions containing 23.5 $\mu$M c-SNAFL, 0.1 mM $HCO_3^-$ and 0.5 M NaCl in order to adjust the carbon dioxide contents of the solutions. The absorbances of the solutions at 490 nm and 540 nm were recorded in order to determine the relationship between these absorbances and the $CO_2$ contents in the solutions.

Figure 10:
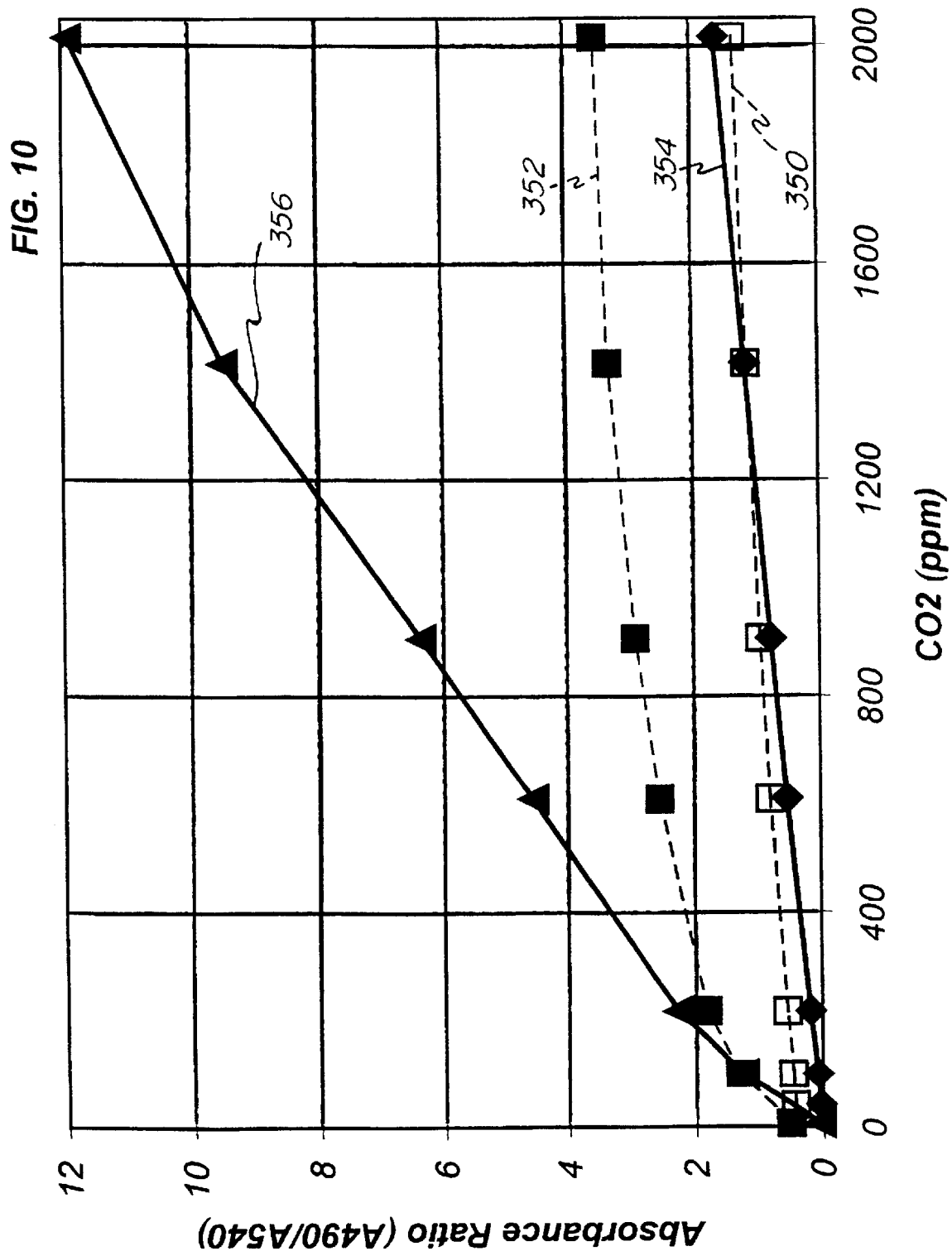
FIG. 10 is a graph comparing the relationships of simple and complex ratios of measured absorbances for dye solutions containing c-SNAFL and $HCO_3^-$ with concentrations of dissolved carbon dioxide bubbled into those solutions.

The relationships between simple and complex ratios of the absorbances of the solutions, on the one hand. and the carbon dioxide contents of the solutions, on the other hand, are shown in FIG. 10. The curve 350 in FIG. 10 represents, for the first batch of solutions, the relationship between simple ratios of the absorbances, $A_{490}/A_{540}$, and the $CO_2$ contents, expressed as ppm. The curve 352 in FIG. 10 represents the analogous relationship for the second batch of solutions. The curves 354 and 356 in FIG. 10 represent the relationship between complex ratios of the absorbances:

$$\frac{A_{490nm} - \frac{(A_{490nm})_{pH\,12}}{(A_{540nm})_{pH\,12}} A_{540nm}}{A_{540nm} - \frac{(A_{540nm})_{pH\,2}}{(A_{490nm})_{pH\,2}} A_{490nm}}$$

and the $CO_2$ contents, expressed as ppm, for the first and second batches, respectively.

The curve 354, which shows the results for the solutions containing 15.6 μM c-SNAFL, 1 mM $HCO_3^-$ and 0.167 M NaCl, manifests a strong linear correlation ($R^2$=0.999) between the complex ratios of the absorbances and the $CO_2$ partial pressures over a range of about 0–2,000 ppm $CO_2$. The curves 354 and 356 each indicate both far stronger linearity and greater sensitivity (that is, a steeper slope) than do the curves 350 and 352, which show the essentially non-linear relationships between the simple ratios of the absorbances and the $CO_2$ partial pressures. These results demonstrate the superiority of the methods for optically determining the partial pressure of carbon dioxide using complex ratios of the absorbances, of the form shown above, over methods using simple ratios of the absorbances.

A comparison of the curves 354 and 356 suggests that the second batch of dye solutions, which contain 0.1 mM $HCO_3^-$, were more sensitive than the dye solution containing 1 mM $HCO_3^-$. As a result of this increased sensitivity, however, curve 354 is linear over larger range of $CO_2$ partial pressures than is curve 356.

In both case, however, the curves 354 and 356 relating the complex ratios to the $CO_2$ contents are closely linear, and show greater sensitivity, than the curves 350 and 352 relating the simple ratios to the $CO_2$ contents. Nonetheless, curves 354 and 356 indicate that the sensitivity of carbon dioxide sensor systems using dye solutions containing c-SNAFL and $HCO_3^-$ can be adjusted in a predictable manner by adjusting the $HCO_3^-$ concentrations in the dye solutions.

EXAMPLE 4

A sensor probe was prepared comprising a sensor housing, an aqueous dye solution containing 50 μM HPTS, 10 mM $HCO_3^-$ and 0.3 M NaCl, a $CO_2$-permeable membrane trapping the aqueous dye solution in the sensor housing, and an optical fiber extending into the housing into optical communication with the aqueous dye solution. Carbon dioxide gas was bubbled into aqueous media to produce test solutions having a range of known $CO_2$ partial pressures. The sensor probe was immersed in each of the test solutions and the dye solution was excited at wavelengths of 405 nm and 460 nm. The fluorescent emission intensities generated when the dye solution was excited at each of these wavelengths were measured and normalized through dividing the fluorescent emission intensities by the respective illumination intensities. The normalized fluorescent emission intensities were compared to the $CO_2$ contents of the test solutions.

Figure 11:
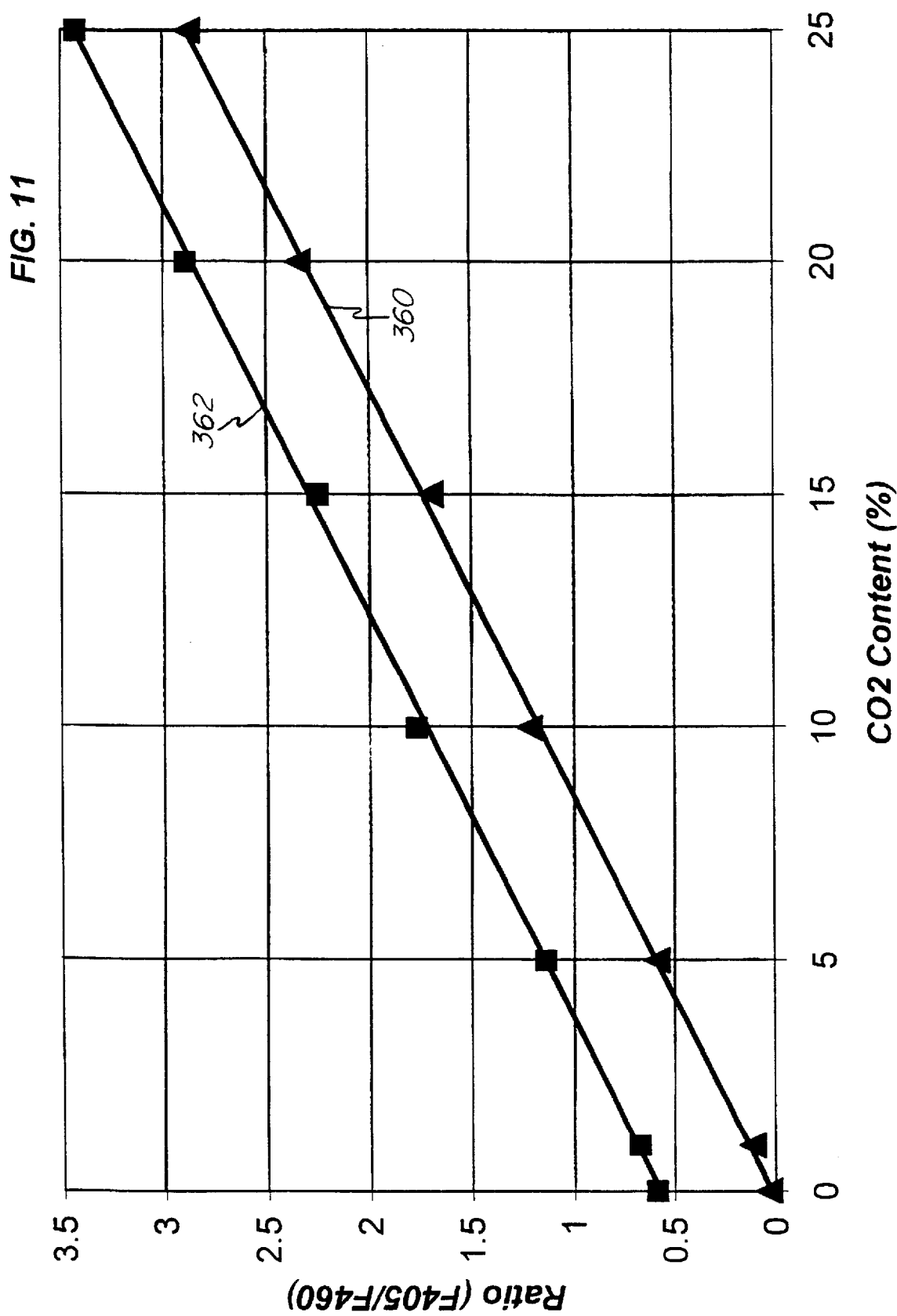
FIG. 11 is a graph comparing the relationships of simple and complex ratios of measured absorbances for dye solutions containing 50 $\mu$M HPTS+10 mM $HCO_3^-$+0.3 M NaCl with $CO_2$ contents of those solutions.

The curve 362 in FIG. 11 shows the relationships between the $CO_2$ contents of the test solutions, on the one hand, and a simple ratio $(F_{405\ nm}/P_{405\ nm})/(F_{460\ nm}/P_{460\ nm})$ on the other. The curve 360 in FIG. 11 shows the relationships between the $CO_2$ contents of the test solutions, on the one hand, and a complex ratio:

$$\frac{F_{405nm}/P_{405nm} - \left[\frac{(F_{405nm}/P_{405nm})_{pH\,12}}{(F_{460nm}/P_{460nm})_{pH\,12}}\right]F_{460nm}/P_{460nm}}{F_{460nm}/P_{460nm} - \left[\frac{(F_{460nm}/P_{460nm})_{pH\,3}}{(F_{405nm}/P_{405nm})_{pH\,3}}\right]F_{405nm}/P_{405nm}}$$

Both of the curves 360 and 362 appear linear throughout the range from 0–25% $CO_2$. As noted earlier, undissociated HPTS molecules do not fluoresce significantly when excited at wavelengths greater than approximately 450 nm. That is, $(F_{460\ nm})_{pH\,3} \approx 0$. Therefore, in the case of a sensor system using HPTS in accordance with the invention, the complex ratio collapses approximately to a linear expression of a simple ratio of the measured fluorescent emission intensities. This explains the parallel results obtained using the simple and complex ratios in this example. The offset between the two curves 360 and 362 is attributable to the ratio $(F_{405\ nm}/P_{405\ nm})_{pH\,12}/(F_{460\ nm}/P_{460\ nm})_{pH\,12}$.

EXAMPLE 5

In order to study the long term stability of a sensor system capable of performing the method of the present invention, a sensor probe was prepared comprising a sensor housing, an aqueous dye solution containing 50 μM HPTS, 20 mM $HCO_3^-$ and 0.3 M NaCl, a $CO_2$-permeable membrane trapping the aqueous dye solution in the sensor housing, and an optical fiber extending into the housing into optical communication with the aqueous dye solution. The sensor probe was autoclaved and exposed to a minimal essential medium which was sparged with 5% $CO_2$ at 37° C. (This is a simulated test for cell culture application.)

Over a period of approximately 14 days, the dye solution was excited by light at a wavelengths of 405 nm and 460 nm. The fluorescent emission intensities generated when the dye solution was excited at each of these wavelengths were measured and normalized through dividing the fluorescent emission intensities by the respective illumination intensities.

Figure 12:
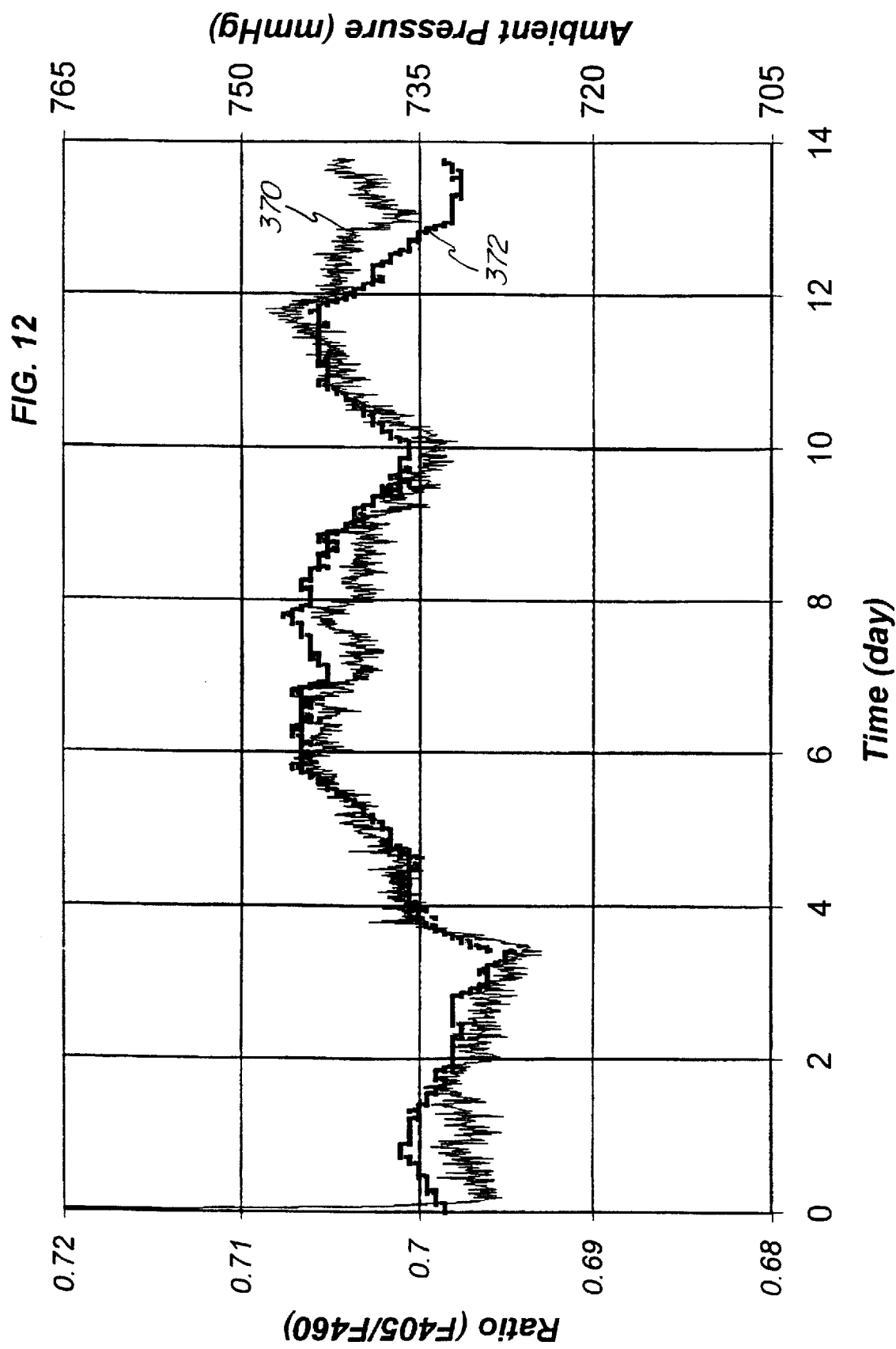
FIG. 12 is a graph comparing the simple ratios of measured fluorescent emission intensities measured in a sensor probe including an aqueous dye solution containing 50 $\mu$M c-SNAFL+20 mM $HCO_3^-$+0.3 M NaCl with the ambient pressure on the medium over a period of 14 days.

The curve 370 in FIG. 12 shows the relationship between elapsed time and the simple ratios $(F_{405\ nm}/P_{405\ nm})/(F_{460\ nm}/P_{460\ nm})$ of the normalized fluorescent emission intensities. The curve 372 shows the ambient pressure as a function of time. A comparison of the curves 370 and 372 shows that the simple ratios track very well with the ambient pressure as the bio-vessel is equilibrated with the ambient pressure. This strong correlation between the simple ratios and the ambient pressure readings indicates that the $CO_2$ sensor measures $CO_2$ partial pressure even at a constant $CO_2$ content of 5%.

EXAMPLE 6

A sensor probe was prepared comprising a sensor housing, an aqueous dye solution containing 46 μM HPTS, 0.4 mM $HCO_3^-$ and 0.5 M NaCl, a $CO_2$-permeable membrane trapping the aqueous dye solution in the sensor housing, and an optical fiber extending into the housing into optical communication with the aqueous dye solution. Carbon dioxide gas was bubbled into aqueous media to produce test solutions having a range of known $CO_2$ partial pressures. The sensor probe was immersed in each of the test solutions and the dye solution was excited at a wavelengths of 480 nm. The intensities of the fluorescent emission were measured at 540 nm and 630 nm, and the resulting intensities were compared to the $CO_2$ contents of the test solutions.

Figure 13:
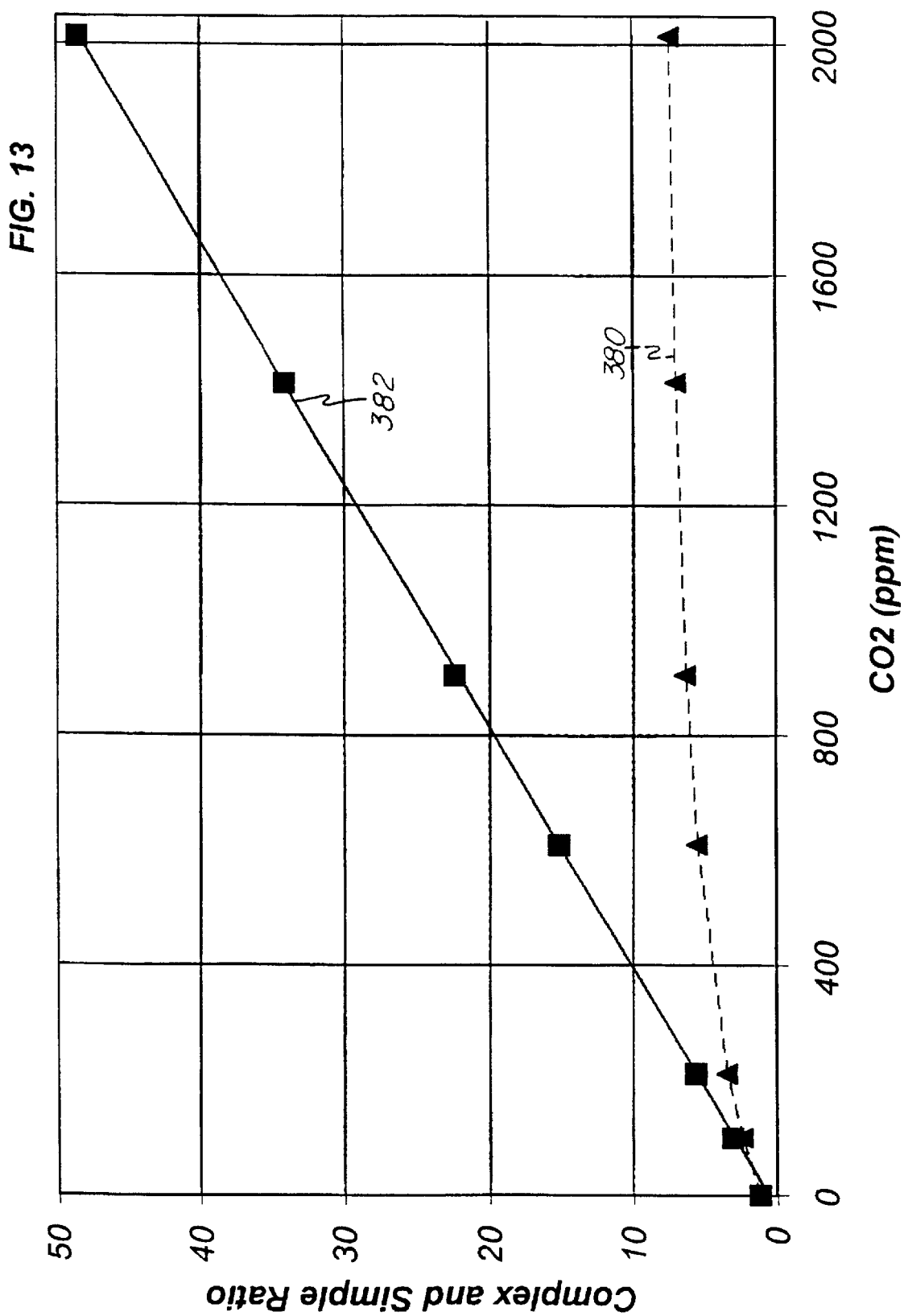
FIG. 13 is a graph comparing the relationships of simple and complex ratios of measured fluorescent emission intensities measured in a sensor probe including an aqueous dye solutions containing 46 $\mu$M c-SNAFL+0.4 mM $HCO_3^-$+0.5 M NaCl with $CO_2$ contents of test solutions.

The results of these measurements are plotted in FIG. 13. Curve 380 in FIG. 13 shows the relationship between the simple ratios $F_{540\ nm}/F_{630\ nm}$ measured for each solution and the known $CO_2$ partial pressures of the solutions. Curve 382 shows the relationship between complex ratios:

$$\frac{F_{540nm} - \frac{(F_{540nm})_{pH\,12}}{(F_{630nm})_{pH\,12}}F_{630nm}}{F_{630nm} - \frac{(F_{630nm})_{pH\,5.5}}{(F_{540nm})_{pH\,5.5}}F_{540nm}}$$

measured for each solution and the $CO_2$ partial pressures of the solutions.

The curve 382 shows strong linearity in the range of 0–2,000 ppm $CO_2$, in marked contrast to the non-linearity of the curve 380 over the same range. Furthermore, the $CO_2$ sensor including an aqueous dye solution containing 46 $\mu$M HPTS, 0.4 mM $HCO_3^-$ and 0.5 M NaCl, combined with the use of the complex ratio, appears to provide a resolution on the order of 1 ppm $CO_2$. This level of resolution is suitable for oceanographic applications.

EXAMPLE 7

In order to study the effect of temperature on a sensor system in accordance with the present invention, a sensor probe was prepared comprising a sensor housing, an aqueous dye solution containing HPTS and $HCO_3^-$, a $CO_2$-permeable membrane trapping the aqueous dye solution in the sensor housing, and an optical fiber extending into the housing into optical communication with the aqueous dye solution. The sensor probe was immersed in a series of solutions containing various dissolved carbon dioxide contents over at temperatures ranging from 1.4° C. to 25° C. The simple ratios of the absorbances of the dye solution at 405 nm and 460 nm were recorded for each temperature and carbon dioxide content.

Figure 14:
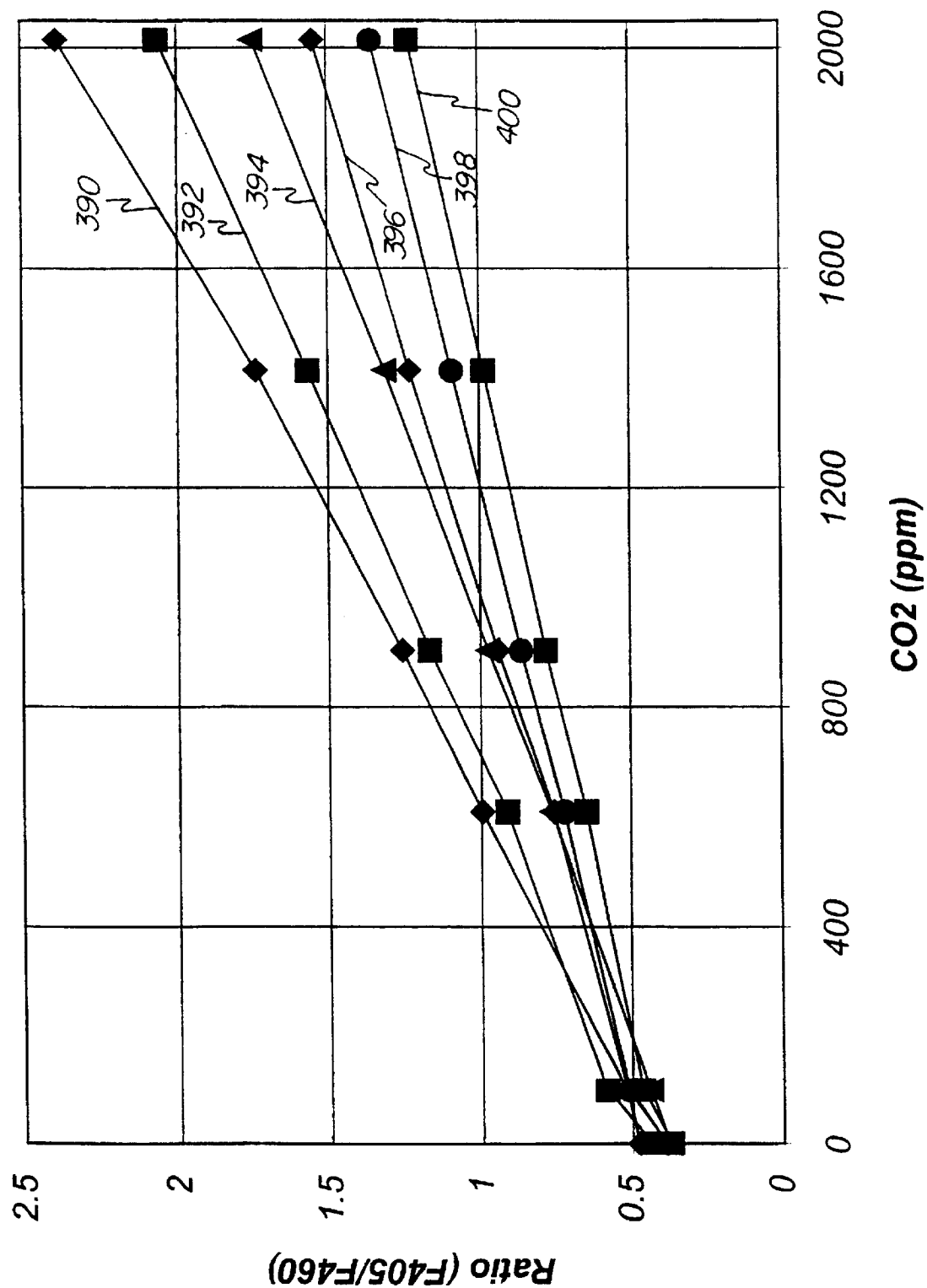
FIG. 14 is a graph showing relationships of simple ratios of measured absorbances for dye solutions containing HPTS and $HCO_3^-$ as functions of $CO_2$ concentration, for a series of temperatures.
Figure 15:
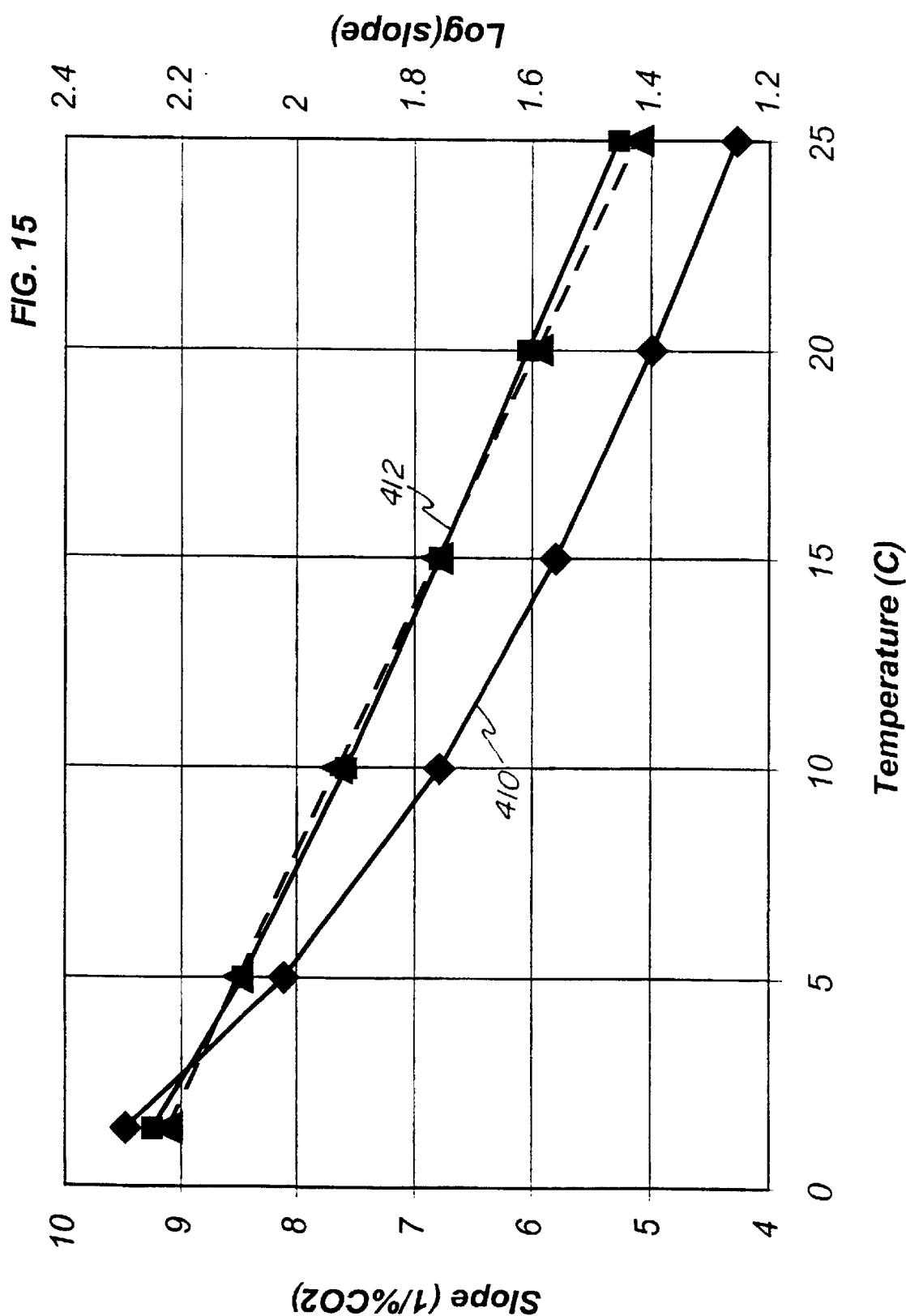
FIG. 15 is a graph showing the slopes of the curves of FIG. 14, plotted as a function of temperature.

The results are shown in FIGS. 14 and 15. Curves 390–400 in FIG. 14 relate the simple ratios of the absorbances to the $CO_2$ concentrations at the following temperatures:

| | |
|---|---|
| Curve 390 | 1.4° C. |
| Curve 392 | 5° C. |
| Curve 394 | 10° C. |
| Curve 396 | 15° C. |
| Curve 398 | 20° C. |
| Curve 400 | 25° C. |

Each of the curves 390–400 shows rough linearity over a range from 0–2,000 ppm $CO_2$.

Curve 410 in FIG. 15 represents the sensitivities (that is, the slopes) of the curves 390–400 of FIG. 14 as a function of temperature. Curve 412 in FIG. 15 represents the logarithm of the sensitivities as a function of temperature. The approximate linearity of curve 412 implies that the sensitivities are an exponential function of the temperatures.

This, in turn, suggests that one may define a temperature coefficient "$\alpha$" such that:

$$\alpha \equiv \frac{1}{S}\frac{\partial S}{\partial T}.$$

where "S" is the sensitivity and "T" is temperature. After integrating:

$$\ln s = \ln A + \alpha T.$$

where "A" is a constant. The curves 410 and 412 are in rough correlation with the equation given immediately above. The temperature coefficient is the slope of the curve 412, which is approximately $\alpha \approx -3.3\%/°C$.

Several factors are believed to contribute to the temperature coefficient of the sensor system. An important factor likely will be the temperature dependence of the equilibrium constants of the dye solution and of the Henry's Law constant. The spectral ratios themselves may be temperature dependent. Changes in the diffusivity of carbon dioxide through the membrane 52 (FIG. 2) also may affect the sensor system's performance, even though the system performs measurements under equilibrium conditions.

EXAMPLE 8

In order to study the long term stability of a sensor system capable of performing the method of the present invention, a sensor probe was prepared comprising a sensor housing, an aqueous dye solution containing 46 $\mu$M c-SNAFL, 0.8 mM $HCO_3^-$ and 0.5 M NaCl, a $CO_2$-permeable membrane trapping the aqueous dye solution in the sensor housing, and an optical fiber extending into the housing into optical communication with the aqueous dye solution. The sensor probe was immersed in a series of test solutions containing various dissolved carbon dioxide concentrations over a period of 800 hours (approximately 33 days). The aqueous dye solution was illuminated at 480 nm and the intensities of the fluorescent emissions from the dye solution were measured at 540 nm and 630 nm.

Figure 16:
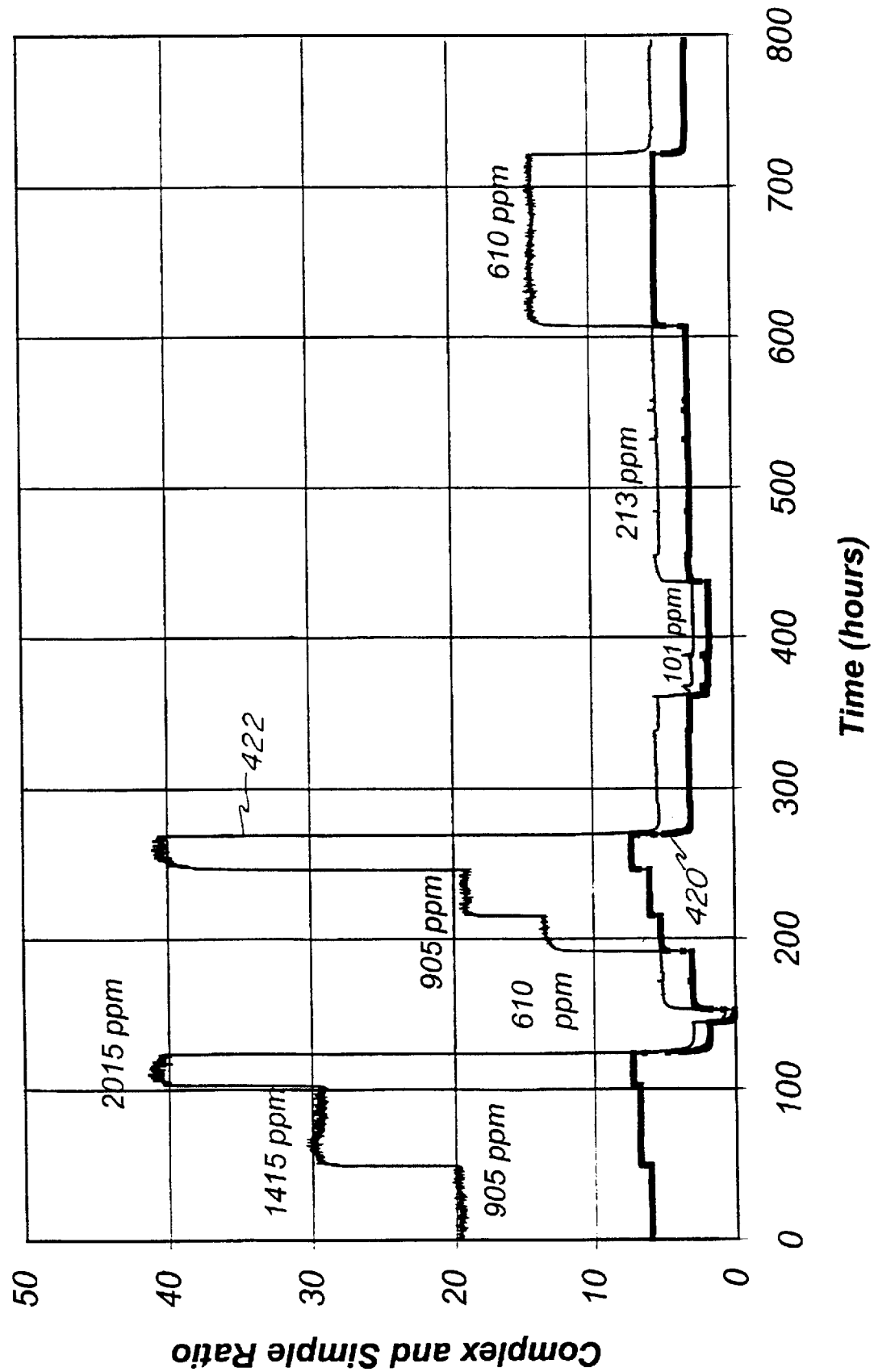
FIG. 16 is a graph comparing simple and complex ratios of measured fluorescent emission intensities measured in a sensor probe including an aqueous dye solution containing 46 $\mu$M c-SNAFL+0.8 mM $HCO_3^-$+0.5 M NaCl at various ppm $CO_2$ contents over a period of 800 hrs. (approximately 33 days).

Curve 420 in FIG. 16 shows the relationship between elapsed time and the simple ratios $F_{540\ nm}/F_{630\ nm}$ of the fluorescent emission intensities. Curve 422 shows the relationship between elapsed time and the complex ratios:

$$\frac{F_{540nm} - \frac{(F_{540nm})_{pH\ 12}}{(F_{630nm})_{pH\ 12}} F_{630nm}}{F_{630nm} - \frac{(F_{630nm})_{pH\ 5.5}}{(F_{540nm})_{pH\ 5.5}} F_{540nm}}$$

of the fluorescent emission intensities.

Curve 422 demonstrates that the sensor system using the complex ratio remained highly stable over 800 hours of continuous use. A comparison of curves 420 and 422 further demonstrates the superior sensitivity achievable using the complex ratios as opposed to the simple ratios FIG. 16 shows the relationship between elapsed time and the simple ratios $F_{540\ nm}/F_{630\ nm}$.

From the foregoing, it will be seen that methods and systems in accordance with the present invention provide highly sensitive measurements of analyte contents, such as pH or $CO_2$ partial pressure, over wide ranges of analyte contents. In particular, it is anticipated that especially preferred methods and systems in accordance with the invention will resolve $CO_2$ partial pressures with resolutions on the order of parts per million over ranges of perhaps as high as 0–2,000 ppm. The sensitivity of these especially preferred systems may be optimized for particular applications by adjusting the $HCO_3^-$ concentrations in the dye solutions. Meanwhile, the long term stability of the methods and systems is improved due to the use of 5 ratiometric expressions to relate the spectral properties of the dye solution to the analyte content.

The preceding description and accompanying drawings are intended to be illustrative of the invention and not limited. Various other modifications and applications will be apparent to one skilled in the art without departing from the true spirit and scope of the invention as defined by the following claims.

What is claimed is:

1. A method for optical chemical sensing of an analyte in a medium, said method comprising the steps of:
   a) exposing a dye solution to the analyte;
   b) illuminating said dye solution to induce a first output light from said dye solution corresponding to a first wavelength and a second output light from said dye solution corresponding to a second wavelength;
   c) measuring an intensity of said first output light to determine a first spectral property "$X_1$" corresponding to said first wavelength;

d) measuring an intensity of said second output light to determine a second spectral property "$X_2$" corresponding to said second wavelength, said first and second spectral properties being selected from the group consisting of absorbances, fluorescent emission intensities and normalized fluorescent emission intensities; and e) determining an analyte content "$Y_{analyte}$" in the medium by means of an expression of the form:

$$Y_{analyte} = f\left(k_1 k_2 \frac{X_1 - k_3 X_2}{X_2 - k_4 X_1}\right),$$

where "f" is a function; and "$k_1$," "$k_2$," "$k_3$" and "$k_4$" are constants.

2. The method as recited in claim 1 for measuring a pH value of the medium, wherein said dye solution is an aqueous solution including an acidic dye having a dissociation constant "$K_a$;" and wherein said step e) includes determining the pH value by means of an expression of the form:

$$pH = pK_a - \log\left(k_2 \frac{X_1 - k_3 X_2}{X_2 - k_4 X_1}\right),$$

where $pK_a \equiv -\log K_a$.

3. The method as recited in claim 1 for measuring a pH value of the medium, wherein:
   said dye solution is an aqueous solution including an acidic dye having a dissociation constant "$K_a$;"
   said step b) includes illuminating said dye solution at said first wavelength to induce said first output light;
   said step b) further includes illuminating said dye solution at said second wavelength to induce said second output light;
   said step c) includes measuring said intensity of said first output light at said first wavelength to determine a first absorbance "$A_1$;"
   said step d) includes measuring said intensity of said second output light at said second wavelength to determine a second absorbance "$A_2$;" and
   said step e) includes determining the pH value by means of an expression of the form:

$$pH = pK_a - \log\left(k_2 \frac{A_1 - k_3 A_2}{A_2 - k_4 A_1}\right),$$

where $pK_a \equiv -\log K_a$.

4. The method as recited in claim 3 for measuring a pH value of the medium, said method comprising the additional steps of:
   f) exposing said dye solution to a low pH buffer solution;
   g) illuminating said dye solution at said first wavelength to induce a first low pH buffer output light;
   h) illuminating said dye solution at said second wavelength to induce a second low pH buffer output light;
   i) measuring an intensity of said first low pH buffer output light at said first wavelength to determine a first low pH buffer absorbance "$(A_1)_{low\,pH}$;"
   j) measuring an intensity of said second low pH buffer output light at said second wavelength to determine a second low pH buffer absorbance "$(A_2)_{low\,pH}$;"
   k) exposing said dye solution to a high pH buffer solution;
   l) illuminating said dye solution at said first wavelength to induce a first high pH buffer output light;
   m) illuminating said dye solution at said second wavelength to induce a second high pH buffer output light;
   n) measuring an intensity of said first high pH buffer output light at said first wavelength to determine a first high pH buffer absorbance "$(A_1)_{high\,pH}$;" and
   o) measuring an intensity of said second high pH buffer output light at said second wavelength to determine a second high pH buffer absorbance "$(A_2)_{high\,pH}$;"
   wherein said step e) includes determining the pH value by means of an expression of the form:

$$pH = pK_a + \log\left(\left[\frac{(A_1)_{low\,pH}}{(A_2)_{high\,pH}}\right] \frac{A_2 - \frac{(A_2)_{low\,pH}}{(A_1)_{low\,pH}} A_1}{A_1 - \frac{(A_1)_{high\,pH}}{(A_2)_{high\,pH}} A_2}\right).$$

5. The method as recited in claim 4 wherein said first wavelength is a peak absorption wavelength of undissociated molecules of said acidic dye and said second wavelength is a peak absorption wavelength of conjugate base ions of said acidic dye.

6. The method as recited in claim 4 wherein said acidic dye is 8-hydroxypyrene-1,3,6-trisulfonic acid; said first wavelength is approximately 403 nm; and said second wavelength is approximately 454 nm.

7. The method as recited in claim 4 wherein said acidic dye is carboxy-seminapthofluorescein; said first wavelength is approximately 490 nm; and said second wavelength is approximately 540 nm.

8. The method as recited in claim 1 for measuring a pH value of the medium, wherein:
   said dye solution is an aqueous solution including an acidic dye having a dissociation constant "$K_a$;"
   said step b) includes illuminating said dye solution at a first intensity "$P_1$" to induce said first output light, and at a second intensity "$P_2$" to induce said second output light;
   said step c) includes measuring an intensity of said first output light to determine a first fluorescent emission intensity "$F_1$;"
   said step d) includes measuring an intensity of said second output light to determine a second fluorescent emission intensity "$F_2$;" and
   said step e) includes determining the pH value by means of an expression of the form:

$$pH = pK_a - \log\left(k_2 \frac{F_1/P_1 - k_3 F_2/P_2}{F_2/P_2 - k_4 F_1/P_1}\right),$$

where $pK_a \equiv -\log K_a$.

9. The method as recited in claim 8 wherein $P_1 = P_2$.

10. The method as recited in claim 8 for measuring a pH value of the medium, said method comprising the additional steps of:
   f) exposing said dye solution to a low pH buffer solution;
   g) illuminating said dye solution at a first low pH buffer intensity "$(P_1)_{low\,pH}$" to induce a first low pH buffer output light from said dye solution corresponding to said first wavelength, and at a second low pH buffer intensity "$(P_2)_{low\,pH}$" to induce a second low pH buffer output light from said dye solution corresponding to said second wavelength;
   h) measuring an intensity of said first low pH buffer output light to determine a first low pH buffer fluorescent emission intensity "$(F_1)_{low\,pH}$;"

i) measuring an intensity of said second low pH buffer output light to determine a second low pH buffer fluorescent emission intensity "$(F_2)_{low\ pH}$;"

j) exposing said dye solution to a high pH buffer solution;

k) illuminating said dye solution at a first high pH buffer intensity "$(P_1)_{high\ pH}$" to induce a first high pH buffer output light from said dye solution corresponding to said first wavelength, and at a second high pH buffer intensity "$(P_2)_{high\ pH}$" to induce a second high pH buffer output light from said dye solution corresponding to said second wavelength;

l) measuring an intensity of said first high pH buffer output light to determine a first high pH buffer fluorescent emission intensity "$(F_1)_{high\ pH}$;" and m) measuring an intensity of said second high pH buffer output light to determine a second high pH buffer fluorescent emission intensity "$(F_2)_{high\ pH}$;"

wherein said step e) includes determining the pH value by means of an expression of the form:

$$pH = pK_a + \log\left(\left[\frac{(F_1/P_1)_{low\,pH}}{(F_2/P_2)_{high\,pH}}\right]\frac{F_2/P_2 - \left[\frac{(F_2/P_2)_{low\,pH}}{(F_1/P_1)_{low\,pH}}\right]F_1/P_1}{F_1/P_1 - \left[\frac{(F_1/P_1)_{high\,pH}}{(F_2/P_2)_{high\,pH}}\right]F_2/P_2}\right).$$

11. The method as recited in claim 10 wherein said first wavelength is a peak excitation wavelength of said acidic dye and said second wavelength is a peak excitation wavelength of a conjugate base of said acidic dye.

12. The method as recited in claim 10 wherein $P_1=P_2$; $(P_1)_{low\ pH}=(P_2)_{low\ pH}$; and $(P_1)_{high\ pH}=(P_2)_{high\ pH}$.

13. The method as recited in claim 10 wherein said acidic dye is 8-hydroxypyrene-1,3,6-trisulfonic acid.

14. The method as recited in claim 10 wherein said acidic dye is carboxy-seminapthofluorescein.

15. The method as recited in claim 1 for measuring a partial pressure of carbon dioxide on the medium, wherein said dye solution is an aqueous solution including $HCO_3^-$ and an acidic dye having a dissociation constant "$K_a$," and wherein said step e) includes determining said partial pressure of carbon dioxide "$P_{CO_2}$" by means of an expression of the form:

$$P_{CO_2} = \frac{K_a}{K_H K_{a1}}[HCO_3^-]\left(k_2\frac{X_1 - k_3 X_2}{X_2 - k_4 X_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

16. The method as recited in claim 1 for measuring a partial pressure of carbon dioxide on the medium, wherein:

said dye solution includes an acidic dye having a dissociation constant "$K_a$;"

said step b) includes illuminating said dye solution at said first wavelength to induce said first output light;

said step b) further includes illuminating said dye solution at said second wavelength to induce said second output light;

said step c) includes measuring said intensity of said first output light at said first wavelength to determine a first absorbance "$A_1$;"

said step d) includes measuring said intensity of said second output at said second wavelength to determine a second absorbance "$A_2$;" and said step e) includes determining said partial pressure of carbon dioxide "$P_{CO_2}$" by means of an expression of the form:

$$P_{CO_2} = \frac{K_a}{K_H K_{a1}}[HCO_3^-]\left(k_2\frac{A_1 - k_3 A_2}{A_2 - k_4 A_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

17. The method as set forth in claim 16 for measuring a partial pressure of carbon dioxide on the medium, said method comprising the additional steps of:

f) exposing said dye solution to a low pH buffer solution;

g) illuminating said dye solution at said first wavelength to induce a first low pH buffer output light;

h) illuminating said dye solution at said second wavelength to induce a second low pH buffer output light;

i) measuring an intensity of said first low pH buffer output light at said first wavelength to determine a first low pH buffer absorbance "$(A_1)_{low\ pH}$;"

j) measuring an intensity of said second low pH buffer output light at said second wavelength to determine a second low pH buffer absorbance "$(A_2)_{low\ pH}$;"

k) exposing said dye solution to a high pH buffer solution;

l) illuminating said dye solution at said first wavelength to induce a first high pH buffer output light;

m) illuminating said dye solution at said second wavelength to induce a second high pH buffer output light;

n) measuring an intensity of said first high pH buffer output light at said first wavelength to determine a first high pH buffer absorbance "$(A_1)_{high\ pH}$;" and o) measuring an intensity of said second high pH buffer output light at said second wavelength to determine a second high pH buffer absorbance "$(A_2)_{high\ pH}$;"

wherein said step e) includes determining said partial pressure of carbon dioxide "$P_{CO_2}$" by means of an expression of the form:

$$P_{CO_2} = \frac{K_a}{K_{a1} K_H}[HCO_3^-]\left(\left[\frac{(A_2)_{high\,pH}}{(A_1)_{low\,pH}}\right]\frac{A_1 - \frac{(A_1)_{high\,pH}}{(A_2)_{high\,pH}}A_2}{A_2 - \frac{(A_2)_{low\,pH}}{(A_1)_{low\,pH}}A_1}\right).$$

18. The method as recited in claim 17 wherein said first wavelength is a peak absorption wavelength of said acidic dye and said second wavelength is a peak absorption wavelength of a conjugate base of said acidic dye.

19. The method as recited in claim 17 wherein said acidic dye is 8-hydroxypyrene-1,3,6-trisulfonic acid; said first wavelength is approximately 403 nm; and said second wavelength is approximately 454 nm.

20. The method as recited in claim 17 wherein said acidic dye is carboxy-seminapthofluorescein; said first wavelength is approximately 490 nm; and said second wavelength is approximately 540 nm.

21. The method as set forth in claim 1 for measuring a partial pressure of carbon dioxide on the medium, wherein:

said dye solution is an aqueous solution including $HCO_3^-$ and an acidic dye having a dissociation constant "$K_a$;"

said step b) includes illuminating said dye solution at a first intensity "$P_1$" to induce said first output light, and at a second intensity "$P_2$" to induce said second output light;

said step c) includes measuring said intensity of said first output light to determine a first fluorescent emission intensity "$F_1$;"

said step d) includes measuring said intensity of said second output light to determine a second fluorescent emission intensity "$F_2$;" and said step e) includes determining said partial pressure of carbon dioxide "$P_{CO_2}$" by means of an expression of the form:

$$P_{CO_2} = \frac{K_a}{K_H K_{a1}}[HCO_3^-]\left(k_2 \frac{F_1/P_1 - k_3 F_2/P_2}{F_2/P_2 - k_4 F_1/P_1}\right),$$

where "$K_H$" is a Henry's Law constant for carbon dioxide in aqueous solution; "$K_{a1}$" is an equilibrium constant for the dissociation of dissolved carbon dioxide to form $HCO_3^-$; and "$[HCO_3^-]$" is a concentration of $HCO_3^-$ in the dye solution.

22. The method as recited in claim 21 wherein $P_1=P_2$.

23. The method as recited in claim 21 for measuring a partial pressure of carbon dioxide on the medium, said method comprising the additional steps of:

f) exposing said dye solution to a low pH buffer solution;

g) illuminating said dye solution at a first low pH buffer intensity "$(P_1)_{low\ pH}$" to induce a first low pH buffer output light from said dye solution corresponding to said first wavelength, and at a second low pH buffer intensity "$(P_2)_{low\ pH}$" to induce a second low pH buffer output light from said dye solution corresponding to said second wavelength;

h) measuring an intensity of said first low pH buffer output light to determine a first low pH buffer fluorescent emission intensity "$(F_1)_{low\ pH}$;"

i) measuring an intensity of said second low pH buffer output light to determine a second low pH buffer fluorescent emission intensity "$(F_2)_{low\ pH}$;"

j) exposing said dye solution to a high pH buffer solution;

k) illuminating said dye solution at a first high pH buffer intensity "$(P_1)_{high\ pH}$" to induce a first high pH buffer output light from said dye solution corresponding to said first wavelength, and at a second high pH buffer intensity "$(P_2)_{high\ pH}$" to induce a second high pH buffer output light from said dye solution corresponding to said second wavelength;

l) measuring an intensity of said first high pH buffer output light to determine a first high pH buffer fluorescent emission intensity "$(F_1)_{high\ pH}$;" and m) measuring an intensity of said second high pH buffer output light to determine a second high pH buffer fluorescent emission intensity "$(F_2)_{high\ pH}$;"

wherein said step e) includes determining said partial pressure of carbon dioxide "$P_{CO_2}$" by means of an expression of the form:

$$P_{CO_2} = \frac{K_a}{K_{a1} K_H}[HCO_3^-]\left(\left[\frac{(F_2/P_2)_{high\ pH}}{(F_1/P_1)_{low\ pH}}\right]\frac{F_1/P_1 - \left[\frac{(F_1/P_1)_{high\ pH}}{(F_2/P_2)_{high\ pH}}\right]F_2/P_2}{F_2/P_2 - \left[\frac{(F_2/P_2)_{low\ pH}}{(F_1/P_1)_{low\ pH}}\right]F_1/P_1}\right).$$

24. The method as recited in claim 23 wherein said first wavelength is a peak excitation wavelength of said acidic dye and said second wavelength is a peak excitation wavelength of a conjugate base of said acidic dye.

25. The method as recited in claim 23 wherein $P_1=P_2$; $(P_1)_{low\ pH}=(P_2)_{low\ pH}$; and $(P_1)_{high\ pH}=(P_2)_{high\ pH}$.

26. The method as recited in claim 23 wherein said acidic dye is 8-hydroxypyrene-1,3,6-trisulfonic acid.

27. The method as recited in claim 23 wherein said acidic dye is carboxy-seminapthofluorescein.

28. A system for optical chemical sensing of an analyte in a medium, said system comprising:

a) a probe containing a dye solution;

b) at least one light source in optical communication with the probe for illuminating the dye material;

c) at least one frequency-sensitive photodetector system for measuring intensities of light output from said probe to determine a first spectral property "$X_1$" of said dye solution corresponding to a first wavelength and a second spectral property "$X_2$" of said dye solution corresponding to a second wavelength; and d) a controller for processing the first and second spectral properties to determine an analyte content "$Y_{analyte}$" in the medium by means of an expression of the form:

$$Y_{analyte} = f\left(k_1 k_2 \frac{X_1 - k_3 X_2}{X_2 - k_4 X_1}\right),$$

where "f" is a function; and "$k_1$," "$k_2$," "$k_3$" and "$k_4$" are constants.

29. The system as recited in claim 28 wherein said controller is a programmed microprocessor.

30. The system as recited in claim 29 wherein said programmed microprocessor is in electrical communication with said at least one light source and said at least one frequency-sensitive photodetector system to modulate said at least one light source and to receive signals from said at least one frequency-sensitive photodetector system representative of said intensities of light output from said probe.

31. The system as recited in claim 29 for measuring a pH value of the medium, wherein said dye solution is an aqueous solution including an acidic dye having a dissociation constant "$K_a$;" and wherein said programmed microprocessor is programmed to determine the pH value by means of an expression of the form:

$$pH = pK_a - \log\left(k_2 \frac{X_1 - k_3 X_2}{X_2 - k_4 X_1}\right),$$

where $pK_a \equiv -\log K_a$.

32. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution at said first wavelength to induce a first output light and a second monochromatic light source for illuminating said dye solution at said second wavelength to induce said second output light;

said at least one frequency-sensitive photodetector system includes a first frequency-sensitive photodetector system for measuring an intensity of said second output light to determine a first absorbance "$A_1$" corresponding to said first wavelength and a second frequency-sensitive photodetector system for measuring an intensity of said second output light to determine a second absorbance "$A_2$" corresponding to said second wavelength; and said programmed microprocessor is programmed to determine the pH value by means of an expression of the form:

$$pH = pK_a - \log\left(k_2 \frac{A_1 - k_3 A_2}{A_2 - k_4 A_1}\right),$$

where $pK_a \equiv -\log K_a$.

33. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution with said first wavelength to induce a first output light and a second monochromatic light source for illuminating said dye solution with said second wavelength to induce said second output light;

said at least one frequency-sensitive photodetector system includes a first frequency-sensitive photodetector system for measuring an intensity of said second output light to determine a first absorbance "$A_1$" corresponding to said first wavelength and a second frequency-sensitive photodetector system for measuring an intensity of said second output light to determine a second absorbance "$A_2$" corresponding to said second wavelength; and said programmed microprocessor is programmed to determine the pH value by means of an expression of the form:

$$pH = pK_a + \log\left\{\left[\frac{(A_1)_{low\,pH}}{(A_2)_{high\,pH}}\right] \frac{A_2 - \frac{(A_2)_{low\,pH}}{(A_1)_{low\,pH}} A_1}{A_1 - \frac{(A_1)_{high\,pH}}{(A_2)_{high\,pH}} A_2}\right\},$$

where $pK_a \equiv -\log K_a$; "$(A_1)_{low\,pH}$" is an absorbance of said dye solution measured when said dye solution is exposed to a low pH buffer solution and illuminated at said first wavelength; "$(A_2)_{low\,pH}$" is an absorbance of said dye solution measured when said dye solution is exposed to the low pH buffer solution and illuminated at said second wavelength; "$(A_1)_{high\,pH}$" is an absorbance of said dye solution measured when said dye solution is exposed to a high pH buffer solution and illuminated at said first wavelength; and "$(A_2)_{high\,pH}$" is an absorbance of said dye solution measured when said dye solution is exposed to the high pH buffer solution and illuminated at said second wavelength.

34. The system as recited in claim 33 wherein said first wavelength is a peak absorption wavelength of said acidic dye and said second wavelength is a peak absorption wavelength of a conjugate base of said acidic dye.

35. The system as recited in claim 33 wherein said acidic dye is 8-hydroxypyrene-1,3,6-trisulfonic acid; said first wavelength is approximately 403 nm; and said second wavelength is approximately 454 nm.

36. The system as recited in claim 33 wherein said acidic dye is carboxy-seminapthofluorescein; said first wavelength is approximately 490 nm; and said second wavelength is approximately 540 nm.

37. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution with a first illuminating light of said first wavelength to induce a first output light and a second monochromatic light source for illuminating said dye solution with a second illuminating light of said second wavelength to induce said second output light;

said system includes a reference photodetector for measuring an intensity "$P_1$" of said first illuminating light and an intensity "$P_2$" of said second illuminating light;

said at least one frequency-sensitive photodetector system includes a first frequency-sensitive photodetector system for measuring said intensities of said second output light to determine a first fluorescent emission intensity "$F_1$" corresponding to said first wavelength and a second fluorescent emission intensity "$F_2$" corresponding to said second wavelength; and said programmed microprocessor is programmed to determine the pH value by means of an expression of the form:

$$pH = pK_a - \log\left(k_2 \frac{F_1/P_1 - k_3 F_2/P_2}{F_2/P_2 - k_4 F_1/P_1}\right),$$

where $pK_a \equiv -\log K_a$.

38. The method as recited in claim 37 wherein said first wavelength is a peak excitation wavelength of said acidic dye and said second wavelength is a peak excitation wavelength of a conjugate base of said acidic dye.

39. The method as recited in claim 37 wherein said acidic dye is 8-hydroxypyrene-1,3,6-trisulfonic acid; said first wavelength is approximately 403 nm; and said second wavelength is approximately 454 nm.

40. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution with a first illuminating light of said first wavelength to induce a first output light and a second monochromatic light source for illuminating said dye solution with a second illuminating light of said second wavelength to induce said second output light;

said system includes a reference photodetector for measuring an intensity "$P_1$" of said first illuminating light and an intensity "$P_2$" of said second illuminating light;

said at least one frequency-sensitive photodetector system includes a first frequency-sensitive photodetector system for measuring said intensities of said second output light to determine a first fluorescent emission intensity "$F_1$" corresponding to said first wavelength and a second fluorescent emission intensity "$F_2$" corresponding to said second wavelength; and said programmed microprocessor is programmed to determine the pH value by means of an expression of the form:

$$pH = pK_a + \log\left\{\left[\frac{(F_1/P_1)_{low\,pH}}{(F_2/P_2)_{high\,pH}}\right]\frac{F_2/P_2 - \left[\frac{(F_2/P_2)_{low\,pH}}{(F_1/P_1)_{low\,pH}}\right]F_1/P_1}{F_1/P_1 - \left[\frac{(F_1/P_1)_{high\,pH}}{(F_2/P_2)_{high\,pH}}\right]F_2/P_2}\right\},$$

where $pK_a \equiv -\log K_a$; "$(F_1/P_1)_{low\,pH}$" is a normalized fluorescent emission intensity of said dye solution measured when said dye solution is exposed to a low pH buffer solution and illuminated at said first wavelength; "$(F_2/P_2)_{low\,pH}$" is a normalized fluorescent emission intensity of said dye solution measured when said dye solution is exposed to the low pH buffer solution and illuminated at said second wavelength; "$(F_1/P_1)_{high\,pH}$" is a normalized fluorescent emission intensity of said dye solution measured when said dye solution is exposed to a high pH buffer solution and illuminated at said first wavelength; and "$(F_2/P_2)_{high\,pH}$" is a normalized fluorescent emission intensity of said dye solution measured when said dye solution is exposed to the high pH buffer solution and illuminated at said second wavelength.

41. The system as recited in claim 40 wherein said first wavelength is a peak excitation wavelength of said acidic dye and said second wavelength is a peak excitation wavelength of a conjugate base of said acidic dye.

42. The system as recited in claim 40 wherein said acidic dye is 8-hydroxypyrene-1,3,6-trisulfonic acid; said first wavelength is approximately 405 nm; and said second wavelength is approximately 460 nm.

43. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution to induce said first and second output light;

said at least one frequency-sensitive photodetector system includes a first frequency-sensitive photodetector system for measuring an intensity of said first output light at said first wavelength to determine a first fluorescent emission intensity "$F_1$" and second frequency-sensitive photodetector system for measuring an intensity of said second output light at said second wavelength to determine a second fluorescent emission intensity "$F_2$;" and said programmed microprocessor is programmed to determine the pH value by means of an expression of the form:

$$pH = pK_a - \log\left(k_2\frac{F_1 - k_3 F_2}{F_2 - k_4 F_1}\right),$$

where $pK_a \equiv -\log K_a$.

44. The system as recited in claim 43 wherein said first wavelength is a peak emission wavelength of said acidic dye and said second wavelength is a peak emission wavelength of a conjugate base of said acidic dye.

45. The system as recited in claim 43 wherein said acidic dye is carboxy-seminapthofluorescein; said first wavelength is approximately 540 nm; and said second wavelength is approximately 630 nm.

46. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution to induce said first and second output light;

said at least one frequency-sensitive photodetector system includes a first frequency-sensitive photodetector system for measuring an intensity of said first output light at said first wavelength to determine a first fluorescent emission intensity "$F_1$" and second frequency-sensitive photodetector system for measuring an intensity of said second output light at said second wavelength to determine a second fluorescent emission intensity "$F_2$;" and said programmed microprocessor is programmed to determine the pH value by means of an expression of the form:

$$pH = pK_a + \log\left\{\left[\frac{(F_1)_{low\,pH}}{(F_2)_{high\,pH}}\right]\frac{F_2 - \left[\frac{(F_2)_{low\,pH}}{(F_1)_{low\,pH}}\right]F_1}{F_1 - \left[\frac{(F_1)_{high\,pH}}{(F_2)_{high\,pH}}\right]F_2}\right\},$$

where $pK_a \equiv -\log K_a$; "$(F_1)_{low\,pH}$" is a fluorescent emission intensity of said dye solution measured when said dye solution is exposed to a low pH buffer solution and illuminated at said first wavelength; "$(F_2)_{low\,pH}$" is a fluorescent emission intensity of said dye solution measured when said dye solution is exposed to the low pH buffer solution and illuminated at said second wavelength; "$(F_1)_{high\,pH}$" is a fluorescent emission intensity of said dye solution measured when said dye solution is exposed to a high pH buffer solution and illuminated at said first wavelength; and "$(F_2)_{high\,pH}$" is a fluorescent emission intensity of said dye solution measured when said dye solution is exposed to the high pH buffer solution and illuminated at said second wavelength.

47. The system as recited in claim 46 wherein said first wavelength is a peak emission wavelength of said acidic dye and said second wavelength is a peak emission wavelength of a conjugate base of said acidic dye.

48. The system as recited in claim 46 wherein said acidic dye is carboxy-seminapthofluorescein; said first wavelength is approximately 540 nm; and said second wavelength is approximately 630 nm.

49. The system as recited in claim 29 for measuring a partial pressure of carbon dioxide on the medium, wherein said dye solution is an aqueous solution including an acidic dye having a dissociation constant "$K_a$;" and wherein said programmed microprocessor is programmed to determine the pH value by means of an expression of the form;

$$P_{CO_2} = \frac{K_a}{K_H K_{a1}}[HCO_3^-]\left(k_2\frac{X_1 - k_3 X_2}{X_2 - k_4 X_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

50. The system as recited in claim 29 for measuring a partial pressure of carbon dioxide on the medium wherein:

said dye solution is an aqueous solution including an acidic dye having a dissociation constant "$K_a$;"

said at least one light source includes a first monochromatic light source for illuminating said dye solution with said first wavelength to induce a first output light and a second monochromatic light source for illuminating said dye solution with said second wavelength to induce said second output light;

said at least one frequency-sensitive photodetector system includes a first frequency-sensitive photodetector system for measuring an intensity of said second output light to determine a first absorbance "$A_1$" corresponding to said first wavelength and a second frequency-sensitive photodetector system for measuring an intensity of said second output light to determine a second absorbance "$A_2$" corresponding to said second wavelength; and said programmed microprocessor is programmed to determine the pH value by means of an expression of the form:

$$P_{CO_2} = \frac{K_a}{K_H K_{a1}}[HCO_3^-]\left(k_2\frac{A_1 - k_3 A_2}{A_2 - k_4 A_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

51. The system as recited in claim 29 for measuring a partial pressure of carbon dioxide on the medium wherein:

said dye solution is an aqueous solution including an acidic dye having a dissociation constant "$K_a$;"

said at least one light source includes a first monochromatic light source for illuminating said dye solution with said first wavelength to induce a first output light and a second monochromatic light source for illuminating said dye solution with said second wavelength to induce said second output light;

said at least one frequency-sensitive photodetector system includes a first frequency-sensitive photodetector system for measuring an intensity of said second output light to determine a first absorbance "$A_1$" corresponding to said first wavelength and a second frequency-sensitive photodetector system for measuring an intensity of said second output light to determine a second absorbance "$A_2$" corresponding to said second wavelength; and said programmed microprocessor is programmed to determine the pH value by means of an expression of the form:

$$P_{CO_2} = \frac{K_a}{K_{a1}K_H}[HCO_3^-]\left(\left(\frac{(A_2)_{high\ pH}}{(A_1)_{low\ pH}}\right)\frac{A_1 - \frac{(A_1)_{high\ pH}}{(A_2)_{high\ pH}}A_2}{A_2 - \frac{(A_2)_{low\ pH}}{(A_1)_{low\ pH}}A_1}\right),$$

where "$K_H$" is a Henry's Law constant for carbon dioxide in aqueous solution; "$K_{a1}$" is an equilibrium constant for the dissociation of dissolved carbon dioxide to form $HCO_3^-$; "$[HCO_3^-]$" is a concentration of $HCO_3^-$ in the dye solution; "$(A_1)_{low\ pH}$" is an absorbance of said dye solution measured when said dye solution is exposed to a low pH buffer solution and illuminated at said first wavelength; "$(A_2)_{low\ pH}$" is an absorbance of said dye solution measured when said dye solution is exposed to the low pH buffer solution and illuminated at said second wavelength;

"$(A_1)_{high\ pH}$" is an absorbance of said dye solution measured when said dye solution is exposed to a high pH buffer solution and illuminated at said first wavelength; and "$(A_2)_{high\ pH}$" is an absorbance of said dye solution measured when said dye solution is exposed to the high pH buffer solution and illuminated at said second wavelength.

52. The system as recited in claim 51 wherein said first wavelength is a peak absorption wavelength of said acidic dye and said second wavelength is a peak absorption wavelength of a conjugate base of said acidic dye.

53. The system as recited in claim 51 wherein said acidic dye is 8-hydroxypyrene-1,3,6-trisulfonic acid; said first wavelength is approximately 403 nm; and said second wavelength is approximately 454 nm.

54. The system as recited in claim 51 wherein said acidic dye is carboxy-seminapthofluorescein; said first wavelength is approximately 490 nm; and said second wavelength is approximately 540 nm.

55. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution with a first illuminating light of said first wavelength to induce a first output light and a second monochromatic light source for illuminating said dye solution with a second illuminating light of said second wavelength to induce said second output light;

said system includes a reference photodetector for measuring an intensity "$P_1$" of said first illuminating light and an intensity "$P_2$" of said second illuminating light;

said at least one frequency-sensitive photodetector system includes a first frequency-sensitive photodetector system for measuring said intensities of said second output light to determine a first fluroescent emission intensity "$F_1$" corresponding to said first wavelength and a second fluorescent emission intensity "$F_2$" corresponding to said second wavelength; and said programmed microprocessor is programmed to determine the pH value by means of an expression of the form:

$$P_{CO_2} = \frac{K_a}{K_H K_{a1}}[HCO_3^-]\left(k_2\frac{F_1/P_1 - k_3 F_2/P_2}{F_2/P_2 - k_4 F_1/P_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

56. The system as recited in claim 55 wherein said first wavelength is a peak excitation wavelength of said acidic dye and said second wavelength is a peak excitation wavelength of a conjugate base of said acidic dye.

57. The system as recited in claim 55 wherein said acidic dye is 8-hydroxypyrene-1,3,6-trisulfonic acid; said first wavelength is approximately 403 nm; and said second wavelength is approximately 454 nm.

58. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution with a first illuminating light of said first wavelength to induce a first output light and a second monochromatic light source for illuminating said dye solution with a second illuminating light of said second wavelength to induce said second output light;

said system includes a reference photodetector for measuring an intensity "$P_1$" of said first illuminating light and an intensity "$P_2$" of said second illuminating light;

said at least one frequency-sensitive photodetector system includes a first frequency-sensitive photodetector system for measuring said intensities of said second output light to determine a first fluorescent emission intensity "$F_1$" corresponding to said first wavelength and a second fluorescent emission intensity "$F_2$" corresponding to said second wavelength; and said programmed microprocessor is programmed to determine the pH value by means of an expression of the form:

$$P_{CO_2} = \frac{K_a}{K_{a1}K_H}[HCO_3^-]\left(\left[\frac{(F_2/P_2)_{high\ pH}}{(F_1/P_1)_{low\ pH}}\right]\frac{F_1/P_1 - \left[\frac{(F_1/P_1)_{high\ pH}}{(F_2/P_2)_{high\ pH}}\right]F_2/P_2}{F_2/P_2 - \left[\frac{(F_2/P_2)_{low\ pH}}{(F_1/P_1)_{low\ pH}}\right]F_1/P_1}\right),$$

where "$K_H$" is a Henry's Law constant for carbon dioxide in aqueous solution; "$K_{a1}$" is an equilibrium constant for the dissociation of dissolved carbon dioxide to form $HCO_3^-$; "$[HCO_3^-]$" is a concentration of $HCO_3^-$ in the dye solution; "$(F_1/P_1)_{low\ pH}$" is a normalized fluorescent emission intensity of said dye solution measured when said dye solution is exposed to a low pH buffer solution and illuminated at said first wavelength; "$(F_2/P_2)_{low\ pH}$" is a normalized fluorescent emission intensity of said dye solution measured when said dye solution is exposed to the low pH buffer solution and illuminated at said second wavelength; "$(F_1/P_1)_{high\ pH}$" is a normalized fluorescent emission intensity of said dye solution measured when said dye solution is exposed to a high pH buffer solution and illuminated at said first wavelength; and "$(F_2/P_2)_{high\ pH}$" is a normalized fluorescent emission intensity of said dye solution measured when said dye solution is exposed to the high pH buffer solution and illuminated at said second wavelength.

59. The system as recited in claim 58 wherein said first wavelength is a peak excitation wavelength of said acidic dye and said second wavelength is a peak excitation wavelength of a conjugate base of said acidic dye.

60. The system as recited in claim 58 wherein said acidic dye is 8-hydroxypyrene-1,3,6-trisulfonic acid; said first wavelength is approximately 405 nm; and said second wavelength is approximately 460 nm.

61. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution to induce said first and second output light;

said at least one frequency-sensitive photodetector system includes a first frequency-sensitive photodetector system for measuring an intensity of said first output light at said first wavelength to determine a first fluorescent emission intensity "$F_1$" and second frequency-sensitive photodetector system for measuring an intensity of said second output light at said second wavelength to determine a second fluorescent emission intensity "$F_2$;" and said programmed microprocessor is programmed to determine the pH value by means of an expression of the form:

$$P_{CO_2} = \frac{K_a}{K_H K_{a1}}[HCO_3^-]\left(k_2\frac{F_1 - k_3 F_2}{F_2 - k_4 F_1}\right),$$

where "$K_H$" is the Henry's Law constant for carbon dioxide in aqueous solution; "$K_{a1}$" is the equilibrium constant for the dissociation of dissolved carbon dioxide to form $HCO_3^-$; and "$[HCO_3^-]$" is the concentration of $HCO_3^-$ in the dye solution.

62. The system as recited in claim 61 wherein said first wavelength is a peak emission wavelength of said acidic dye and said second wavelength is a peak emission wavelength of a conjugate base of said acidic dye.

63. The system as recited in claim 61 wherein said acidic dye is carboxy-seminapthofluorescein; said first wavelength is approximately 540 nm; and said second wavelength is approximately 630 nm.

64. The system as recited in claim 29 for measuring a pH value of the medium wherein:

said dye solution is an aqueous solution including an acidic dye having a dissociation constant "$K_a$;"

said at least one light source includes a first monochromatic light source for illuminating said dye solution to induce said first and second output light;

said at least one frequency-sensitive photodetector system includes a first frequency-sensitive photodetector system for measuring an intensity of said first output light at said first wavelength to determine a first fluorescent emission intensity "$F_1$" and second frequency-sensitive photodetector system for measuring an intensity of said second output light at said second wavelength to determine a second fluorescent emission intensity "$F_2$;" and said programmed microprocessor is programmed to determine the pH value by means of an expression of the form:

$$P_{CO_2} = \frac{K_a}{K_{a1}K_H}[HCO_3^-]\left(\left[\frac{(F_2)_{high\ pH}}{(F_1)_{low\ pH}}\right]\frac{F_1 - \left[\frac{(F_1)_{high\ pH}}{(F_2)_{high\ pH}}\right]F_2}{F_2 - \left[\frac{(F_2)_{low\ pH}}{(F_1)_{low\ pH}}\right]F_1}\right),$$

where "$K_H$" is a Henry's Law constant for carbon dioxide in aqueous solution; "$K_{a1}$" is an equilibrium constant for the dissociation of dissolved carbon dioxide to form $HCO_3^-$; "$[HCO_3^-]$" is a concentration of $HCO_3^-$ in the dye solution; "$(F_1)_{low\ pH}$" is a fluorescent emission intensity of said dye solution measured when said dye solution is exposed to a low pH buffer solution and illuminated at said first wavelength; "$(F_2)_{low\ pH}$" is a fluorescent emission intensity of said dye solution measured when said dye solution is exposed to the low pH buffer solution and illuminated at said second wavelength; "$(F_1)_{high\ pH}$" is a fluorescent emission intensity of said dye solution measured when said dye solution is exposed to a high pH buffer solution and illuminated at said first wavelength; and "$(F_2)_{high\ pH}$" is a fluorescent emission intensity of said dye solution measured when said dye solution is exposed to the high pH buffer solution and illuminated at said second wavelength.

65. The system as recited in claim 64 wherein said first wavelength is a peak emission wavelength of said acidic dye and said second wavelength is a peak emission wavelength of a conjugate base of said acidic dye.

66. The system as recited in claim 64 wherein said acidic dye is 8-hydroxypyrene-1,3,6-trisulfonic acid; said first wavelength is approximately 403 nm; and said second wavelength is approximately 454 nm.

* * * * *